US008980292B2

(12) United States Patent
Dihora et al.

(10) Patent No.: US 8,980,292 B2
(45) Date of Patent: *Mar. 17, 2015

(54) CONDITIONER COMPOSITIONS WITH INCREASED DEPOSITION OF POLYACRYLATE MICROCAPSULES

(75) Inventors: Jiten Odhavji Dihora, Hamilton, OH (US); Jun Hasegawa, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/439,475

(22) Filed: Apr. 4, 2012

(65) Prior Publication Data

US 2012/0282309 A1  Nov. 8, 2012

Related U.S. Application Data

(60) Provisional application No. 61/472,860, filed on Apr. 7, 2011.

(51) Int. Cl.
*A61K 8/02* (2006.01)
*A01N 25/34* (2006.01)
*A61K 9/16* (2006.01)
*A61K 8/87* (2006.01)
*A61K 8/11* (2006.01)
*A61Q 5/12* (2006.01)
*A61Q 13/00* (2006.01)

(52) U.S. Cl.
CPC ... *A61K 8/87* (2013.01); *A61K 8/11* (2013.01); *A61Q 5/12* (2013.01); *A61Q 13/00* (2013.01); *A61K 2800/412* (2013.01); *A61K 2800/5424* (2013.01)
USPC ............ 424/401; 424/408; 424/417; 424/490

(58) Field of Classification Search
None
See application file for complete search history.

(56) References Cited

U.S. PATENT DOCUMENTS

| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,730,456 A | 1/1956 | Green et al. |
| 2,730,457 A | 1/1956 | Green et al. |
| 2,800,457 A | 7/1957 | Green et al. |
| 2,800,458 A | 7/1957 | Green |
| 2,809,971 A | 10/1957 | Bernstein et al. |
| 2,826,551 A | 3/1958 | Geen |
| RE24,899 E | 11/1960 | Green |
| 3,236,733 A | 2/1966 | Karsten et al. |
| 3,332,880 A | 7/1967 | Kessler et al. |
| 3,429,827 A | 2/1969 | Ruus |
| 3,516,941 A | 6/1970 | Matson |
| 3,660,304 A | 5/1972 | Matsukawa et al. |
| 3,681,248 A | 8/1972 | Gould et al. |
| 3,691,140 A | 9/1972 | Silver |
| 3,753,196 A | 8/1973 | Kurtz et al. |
| 3,761,418 A | 9/1973 | Parran, Jr. |
| 3,772,215 A | 11/1973 | Gould et al. |
| 3,826,756 A | 7/1974 | Bachmann et al. |
| 3,886,085 A | 5/1975 | Kiritani et al. |
| 3,898,039 A | 8/1975 | Lin |
| 3,929,678 A | 12/1975 | Laughlin et al. |
| 3,958,581 A | 5/1976 | Abegg et al. |
| 3,962,418 A | 6/1976 | Birkofer |
| 3,964,500 A | 6/1976 | Drakoff |
| 3,965,033 A | 6/1976 | Matsukawa et al. |
| 4,001,140 A | 1/1977 | Foris et al. |
| 4,046,750 A | 9/1977 | Rembaum |
| 4,062,799 A | 12/1977 | Matsukawa et al. |
| 4,075,134 A | 2/1978 | Morehouse, Jr. et al. |
| 4,081,376 A | 3/1978 | Strub |
| 4,087,376 A | 5/1978 | Foris et al. |
| 4,089,802 A | 5/1978 | Foris et al. |
| 4,093,556 A | 6/1978 | Wojciak |
| 4,100,103 A | 7/1978 | Foris et al. |
| 4,105,823 A | 8/1978 | Hasler et al. |
| 4,145,184 A | 3/1979 | Brain et al. |
| 4,166,152 A | 8/1979 | Baker et al. |
| 4,183,911 A | 1/1980 | Smithies et al. |
| 4,197,346 A | 4/1980 | Stevens |
| 4,197,865 A | 4/1980 | Jacquet et al. |
| 4,217,914 A | 8/1980 | Jacquet et al. |

(Continued)

FOREIGN PATENT DOCUMENTS

| CA | 2306397 A1 | 10/2000 |
| CN | 101088567 | 12/2007 |

(Continued)

OTHER PUBLICATIONS

Zhang, Z.; Sun, G.; "Mechanical Properties of Melamine-Formaldehyde microcapsules," J. Microencapsulation, vol. 18, No. 5, pp. 593-602, 2001.
PCT International Search Report and Written Opinion dated Nov. 27, 2012, PCT/US2012/032076.
PCT International Search Report and Written Opinion dated Nov. 27, 2012, PCT/US2012/032101.
PCT International Search Report and Written Opinion dated Nov. 27, 2012, PCT/US2012/032065.
Zim's Crack Creme (R), 2003, Perfects Products, Inc., Berlin Center, Ohio 44401.
International Search Report for PCT/US2005/020223, mailed May 10, 2005, 4 pages.
International Search Report for PCT/IB2010/052127, mailed May 12, 2011, 5 pages.
International Search Report for PCT/IB2010/052128, mailed Dec. 28, 2010, 3 pages.
International Search Report for PCT/IB2010/052121 mailed Feb. 16, 2011, 3 pages.

(Continued)

*Primary Examiner* — Susan Tran
(74) *Attorney, Agent, or Firm* — Carlos A. Garcia; James T. Fondriest

(57) ABSTRACT

A conditioner composition that increases the deposition and retention of benefit agent containing polyacrylate microcapsules onto hair. The conditioner composition is based on the combination of anionic charged polyacrylate microcapsules, deposition aids, conditioner agents, and a carrier.

19 Claims, No Drawings

(56) References Cited

U.S. PATENT DOCUMENTS

| | | |
|---|---|---|
| 4,221,710 A | 9/1980 | Hoshi et al. |
| 4,234,627 A | 11/1980 | Schilling |
| 4,240,450 A | 12/1980 | Grollier et al. |
| 4,247,411 A | 1/1981 | Vanierberghe et al. |
| 4,251,386 A | 2/1981 | Saeki et al. |
| 4,275,055 A | 6/1981 | Nachtigal et al. |
| 4,285,720 A | 8/1981 | Scher |
| 4,323,683 A | 4/1982 | Bolich, Jr. et al. |
| 4,345,080 A | 8/1982 | Bolich, Jr. |
| 4,356,109 A | 10/1982 | Saeki et al. |
| 4,364,837 A | 12/1982 | Pader |
| 4,379,753 A | 4/1983 | Bolich, Jr. |
| 4,381,919 A | 5/1983 | Jacquet et al. |
| 4,422,853 A | 12/1983 | Jacquet et al. |
| 4,423,099 A | 12/1983 | Mueller et al. |
| 4,428,869 A | 1/1984 | Munteanu et al. |
| 4,430,243 A | 2/1984 | Bragg |
| 4,444,699 A | 4/1984 | Hayford |
| 4,446,032 A | 5/1984 | Munteanu et al. |
| 4,450,123 A | 5/1984 | Egawa et al. |
| 4,470,982 A | 9/1984 | Winkler |
| 4,507,280 A | 3/1985 | Pohl et al. |
| 4,515,705 A | 5/1985 | Moeddel |
| 4,529,586 A | 7/1985 | De Marco et al. |
| 4,537,706 A | 8/1985 | Severson, Jr. |
| 4,537,707 A | 8/1985 | Severson, Jr. |
| 4,547,429 A | 10/1985 | Greiner et al. |
| 4,550,862 A | 11/1985 | Barker et al. |
| 4,552,811 A | 11/1985 | Brown et al. |
| 4,561,997 A | 12/1985 | Roehl |
| 4,561,998 A | 12/1985 | Wertz et al. |
| 4,574,110 A | 3/1986 | Asano et al. |
| 4,588,639 A | 5/1986 | Ozono |
| 4,597,898 A | 7/1986 | Vander Meer |
| 4,601,863 A | 7/1986 | Shioi et al. |
| 4,608,250 A | 8/1986 | Jacquet et al. |
| 4,610,927 A | 9/1986 | Irgarashi et al. |
| 4,622,267 A | 11/1986 | Riecke |
| 4,663,158 A | 5/1987 | Wolfram et al. |
| 4,708,924 A | 11/1987 | Nagai et al. |
| 4,719,099 A | 1/1988 | Grollier et al. |
| 4,722,865 A | 2/1988 | Huizer |
| 4,741,855 A | 5/1988 | Grote et al. |
| 4,746,467 A | 5/1988 | Sakamoto et al. |
| 4,775,656 A | 10/1988 | Harada et al. |
| 4,780,370 A | 10/1988 | Pointier |
| 4,798,691 A | 1/1989 | Kasai et al. |
| 4,803,947 A | 2/1989 | Ueki et al. |
| 4,824,707 A | 4/1989 | Spector |
| 4,863,626 A | 9/1989 | Coyne et al. |
| 4,865,759 A | 9/1989 | Coyne et al. |
| 4,882,220 A | 11/1989 | Ono et al. |
| 4,908,271 A | 3/1990 | Kasai et al. |
| 4,911,851 A | 3/1990 | Ladd, Jr. et al. |
| 4,917,920 A | 4/1990 | Ono et al. |
| 4,919,841 A | 4/1990 | Kamel et al. |
| 4,957,666 A | 9/1990 | Kawamura et al. |
| 4,968,451 A | 11/1990 | Scheibel et al. |
| 4,972,000 A | 11/1990 | Kawashima et al. |
| 5,009,880 A | 4/1991 | Grollier et al. |
| 5,061,410 A | 10/1991 | Sakamoto et al. |
| 5,066,419 A | 11/1991 | Walley et al. |
| 5,071,706 A | 12/1991 | Soper |
| 5,104,646 A | 4/1992 | Bolich, Jr. et al. |
| 5,105,823 A | 4/1992 | Blum |
| 5,106,609 A | 4/1992 | Bolich, Jr. et al. |
| 5,113,585 A | 5/1992 | Rogers et al. |
| 5,118,756 A | 6/1992 | Asano et al. |
| 5,120,349 A | 6/1992 | Stewart et al. |
| 5,137,646 A | 8/1992 | Schmidt et al. |
| 5,145,675 A | 9/1992 | Won |
| 5,176,903 A | 1/1993 | Goldberg et al. |
| 5,185,155 A | 2/1993 | Behan et al. |
| 5,188,753 A | 2/1993 | Schmidt et al. |
| 5,225,278 A | 7/1993 | Kielbania, Jr. et al. |
| 5,232,613 A | 8/1993 | Bacon et al. |
| 5,232,769 A | 8/1993 | Yamato et al. |
| 5,234,611 A | 8/1993 | Trinh et al. |
| 5,234,682 A | 8/1993 | Macchio et al. |
| 5,277,979 A | 1/1994 | Kielbania, Jr. et al. |
| 5,278,106 A | 1/1994 | Nakashima et al. |
| 5,292,835 A | 3/1994 | Jahns et al. |
| RE34,584 E | 4/1994 | Grote et al. |
| 5,324,444 A | 6/1994 | Berry et al. |
| 5,342,556 A | 8/1994 | Traubel et al. |
| 5,362,565 A | 11/1994 | Murano et al. |
| 5,366,652 A | 11/1994 | Capeci et al. |
| 5,370,881 A | 12/1994 | Fuisz |
| 5,380,756 A | 1/1995 | Andrews et al. |
| 5,407,609 A | 4/1995 | Tice et al. |
| 5,468,473 A | 11/1995 | Mullen |
| 5,486,303 A | 1/1996 | Capeci et al. |
| 5,487,884 A | 1/1996 | Bissett et al. |
| 5,489,392 A | 2/1996 | Capeci et al. |
| 5,516,448 A | 5/1996 | Capeci et al. |
| 5,565,145 A | 10/1996 | Watson et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,580,578 A | 12/1996 | Oshlack et al. |
| 5,595,967 A | 1/1997 | Miracle et al. |
| 5,596,051 A | 1/1997 | Jahns et al. |
| 5,597,936 A | 1/1997 | Perkins et al. |
| 5,607,980 A | 3/1997 | McAtee et al. |
| 5,611,972 A | 3/1997 | Tararuj et al. |
| 5,637,401 A | 6/1997 | Berman et al. |
| 5,648,328 A | 7/1997 | Angell et al. |
| 5,652,228 A | 7/1997 | Bissett |
| 5,656,584 A | 8/1997 | Angell et al. |
| 5,674,478 A | 10/1997 | Dodd et al. |
| 5,681,852 A | 10/1997 | Bissett |
| 5,691,297 A | 11/1997 | Nassano et al. |
| 5,702,714 A | 12/1997 | Goss |
| 5,716,938 A | 2/1998 | Provitt |
| 5,723,420 A | 3/1998 | Wei et al. |
| 5,725,869 A | 3/1998 | Lo |
| 5,750,122 A | 5/1998 | Evans et al. |
| 5,756,436 A | 5/1998 | Royce et al. |
| 5,759,573 A | 6/1998 | Kim |
| 5,782,409 A | 7/1998 | Paul |
| 5,783,536 A | 7/1998 | Farrell et al. |
| 5,800,805 A | 9/1998 | Salas |
| 5,807,956 A | 9/1998 | Czech |
| 5,827,538 A | 10/1998 | Cussler et al. |
| 5,833,971 A | 11/1998 | Baldwin |
| 5,856,409 A | 1/1999 | Ziemelis et al. |
| 5,876,755 A | 3/1999 | Perring et al. |
| 5,879,584 A | 3/1999 | Bianchetti et al. |
| 5,885,701 A | 3/1999 | Berman et al. |
| 5,929,022 A | 7/1999 | Velazquez |
| 5,945,085 A | 8/1999 | Salas et al. |
| 5,962,018 A | 10/1999 | Curtis et al. |
| 5,972,859 A | 10/1999 | Farrell et al. |
| 5,981,681 A | 11/1999 | Czech |
| 6,024,943 A | 2/2000 | Ness et al. |
| D424,745 S | 5/2000 | Tseng et al. |
| 6,075,003 A | 6/2000 | Haq et al. |
| 6,159,485 A | 12/2000 | Yu et al. |
| 6,182,365 B1 | 2/2001 | Tseng et al. |
| 6,185,822 B1 | 2/2001 | Tseng et al. |
| 6,194,375 B1 | 2/2001 | Ness et al. |
| 6,207,782 B1 | 3/2001 | Czech et al. |
| 6,221,326 B1 | 4/2001 | Amiche |
| 6,221,826 B1 | 4/2001 | Surutzidis et al. |
| 6,225,464 B1 | 5/2001 | Hiler, II et al. |
| 6,228,398 B1 | 5/2001 | Devane et al. |
| 6,235,274 B1 | 5/2001 | Lou et al. |
| 6,235,773 B1 | 5/2001 | Bissett |
| 6,245,366 B1 | 6/2001 | Popplewell et al. |
| 6,245,733 B1 | 6/2001 | Mosbaugh |
| 6,248,364 B1 | 6/2001 | Sengupta et al. |
| 6,258,857 B1 | 7/2001 | Iijima et al. |
| 6,294,514 B1 | 9/2001 | Welling |

(56) References Cited

U.S. PATENT DOCUMENTS

| | | |
|---|---|---|
| 6,298,558 B1 | 10/2001 | Tseng et al. |
| 6,306,812 B1 | 10/2001 | Perkins et al. |
| 6,325,995 B1 | 12/2001 | El-Nokaly et al. |
| 6,326,348 B1 | 12/2001 | Vinson et al. |
| 6,329,057 B1 | 12/2001 | Dungworth et al. |
| 6,348,218 B1 | 2/2002 | Hed et al. |
| 6,362,159 B1 | 3/2002 | Aguadisch et al. |
| 6,368,633 B1 | 4/2002 | Lou et al. |
| 6,375,872 B1 | 4/2002 | Chao |
| 6,375,983 B1 | 4/2002 | Kantor et al. |
| 6,399,192 B1 | 6/2002 | Pinna et al. |
| 6,428,796 B1 | 8/2002 | Gers-Barlag et al. |
| 6,451,754 B1 | 9/2002 | Rowland et al. |
| 6,482,969 B1 | 11/2002 | Helmrick et al. |
| 6,489,047 B2 | 12/2002 | Mosbaugh |
| 6,498,135 B1 | 12/2002 | Angell et al. |
| 6,503,495 B1 | 1/2003 | Alwattari et al. |
| 6,531,156 B1 | 3/2003 | Clark et al. |
| 6,558,706 B2 | 5/2003 | Kantor et al. |
| 6,592,990 B2 | 7/2003 | Schwantes |
| 6,594,904 B1 | 7/2003 | Tseng |
| 6,607,717 B1 | 8/2003 | Johnson et al. |
| 6,608,017 B1 | 8/2003 | Dihora et al. |
| 6,638,591 B2 | 10/2003 | Bowen et al. |
| 6,670,311 B1 | 12/2003 | Aldcroft et al. |
| 6,682,749 B1 | 1/2004 | Potechin et al. |
| 6,696,049 B2 | 2/2004 | Vatter et al. |
| 6,696,400 B2 | 2/2004 | Puelle Andrade et al. |
| 6,703,032 B2 | 3/2004 | Gers-Barlag et al. |
| 6,730,325 B2 | 5/2004 | Devane et al. |
| 6,733,790 B1 | 5/2004 | Garces Garces |
| 6,767,880 B1 | 7/2004 | Foley et al. |
| 6,769,271 B2 | 8/2004 | Mosbaugh |
| 6,770,293 B2 | 8/2004 | Angel et al. |
| 6,780,507 B2 | 8/2004 | Toreki et al. |
| 6,783,770 B2 | 8/2004 | Angel et al. |
| 6,790,814 B1 | 9/2004 | Marin et al. |
| 6,793,936 B2 | 9/2004 | Devane et al. |
| 6,797,683 B2 | 9/2004 | Shana'a et al. |
| 6,800,598 B1 | 10/2004 | Waeschenbach et al. |
| 6,806,249 B2 | 10/2004 | Yang et al. |
| 6,846,785 B2 | 1/2005 | Patel |
| 6,849,584 B2 * | 2/2005 | Geary et al. ............. 510/119 |
| 6,849,591 B1 | 2/2005 | Boeckh et al. |
| 6,864,223 B2 | 3/2005 | Smith et al. |
| 6,869,923 B1 | 3/2005 | Cunningham et al. |
| 6,872,853 B1 | 3/2005 | Van Der Schaaf et al. |
| 6,881,482 B2 | 4/2005 | Vasisht |
| 6,902,742 B2 | 6/2005 | Devane |
| 6,916,481 B1 | 7/2005 | Prud'Homme et al. |
| 6,939,992 B2 | 9/2005 | Van Der Schaaf et al. |
| 6,944,952 B1 | 9/2005 | Tseng |
| 6,951,836 B2 | 10/2005 | Jahns et al. |
| 6,955,823 B2 | 10/2005 | Casson et al. |
| 6,958,313 B2 | 10/2005 | Caswell et al. |
| 6,982,256 B2 | 1/2006 | Votteler et al. |
| 7,015,186 B2 | 3/2006 | Aussant et al. |
| 7,041,767 B2 | 5/2006 | Lange et al. |
| 7,053,034 B2 | 5/2006 | Shefer et al. |
| 7,069,658 B2 | 7/2006 | Tseng |
| 7,105,064 B2 | 9/2006 | Popplewell et al. |
| 7,119,057 B2 | 10/2006 | Popplewell et al. |
| 7,122,512 B2 | 10/2006 | Brain et al. |
| 7,125,835 B2 | 10/2006 | Bennett et al. |
| 7,137,570 B2 | 11/2006 | Wheatley et al. |
| 7,159,792 B2 | 1/2007 | Wheatley et al. |
| 7,186,679 B2 | 3/2007 | Shepherd, Jr. |
| 7,186,680 B2 | 3/2007 | Caswell et al. |
| 7,192,599 B2 | 3/2007 | Mercier et al. |
| 7,196,049 B2 | 3/2007 | Brain et al. |
| 7,204,998 B2 | 4/2007 | Holzner et al. |
| 7,208,463 B2 | 4/2007 | Heltovics et al. |
| 7,208,465 B2 | 4/2007 | Heltovics et al. |
| 7,211,273 B2 | 5/2007 | Hsu |
| 7,211,556 B2 | 5/2007 | Heibel et al. |
| 7,217,777 B2 | 5/2007 | Lange et al. |
| 7,226,607 B2 | 6/2007 | Uchiyama et al. |
| 7,229,611 B2 | 6/2007 | Zamudio-Tena et al. |
| 7,235,261 B2 | 6/2007 | Smith et al. |
| 7,241,835 B2 | 7/2007 | O'Brien et al. |
| 7,247,374 B2 | 7/2007 | Haggquist |
| 7,270,828 B2 | 9/2007 | Masuda et al. |
| 7,279,542 B2 | 10/2007 | Ouali et al. |
| 7,293,719 B2 | 11/2007 | Wheatley et al. |
| 7,294,612 B2 | 11/2007 | Popplewell et al. |
| 7,311,900 B2 | 12/2007 | Conover |
| 7,338,928 B2 | 3/2008 | Lau et al. |
| 7,375,875 B2 | 5/2008 | Whitesides et al. |
| 7,381,417 B2 | 6/2008 | Gamez-Garcia |
| 7,399,324 B2 | 7/2008 | Roddenbery et al. |
| 7,407,650 B2 | 8/2008 | Heltovics et al. |
| 7,413,731 B2 | 8/2008 | Heltovics et al. |
| 7,442,838 B2 | 10/2008 | Van Der Schaaf et al. |
| 7,452,547 B2 | 11/2008 | Lambino et al. |
| 7,465,439 B2 | 12/2008 | Avery et al. |
| 7,491,687 B2 | 2/2009 | Popplewell et al. |
| 7,521,124 B2 | 4/2009 | Ahn et al. |
| 7,524,807 B2 | 4/2009 | Clapp et al. |
| 7,532,388 B2 | 5/2009 | Whitesides et al. |
| 7,538,077 B2 | 5/2009 | Sichmann et al. |
| 7,538,078 B2 | 5/2009 | Holzner et al. |
| 7,569,528 B2 | 8/2009 | Lant et al. |
| 7,575,633 B2 | 8/2009 | Romanin |
| 7,575,804 B2 | 8/2009 | Lang-Wittkowski et al. |
| 7,585,824 B2 | 9/2009 | Popplewell et al. |
| 7,585,825 B2 | 9/2009 | Artiga Gonzalez et al. |
| 7,585,832 B2 | 9/2009 | Smith et al. |
| 7,736,695 B2 | 6/2010 | Schwantes et al. |
| 7,794,836 B2 | 9/2010 | Vasishtha et al. |
| 7,799,421 B2 | 9/2010 | Goodson et al. |
| 7,799,752 B2 | 9/2010 | Ness et al. |
| 7,803,422 B2 | 9/2010 | Schwantes et al. |
| 7,833,960 B2 | 11/2010 | Lei et al. |
| 7,871,588 B2 | 1/2011 | Lindner et al. |
| 7,985,445 B2 | 7/2011 | Schwantes et al. |
| 8,022,029 B2 | 9/2011 | Broze et al. |
| 8,026,205 B2 | 9/2011 | Broze et al. |
| 8,053,405 B2 | 11/2011 | Narayanan et al. |
| 8,067,089 B2 | 11/2011 | Schwantes |
| 8,071,214 B2 | 12/2011 | Schwantes |
| 8,093,201 B2 | 1/2012 | Broze et al. |
| 8,110,284 B2 | 2/2012 | Naigertsik et al. |
| 8,119,163 B2 | 2/2012 | Devane et al. |
| 8,129,327 B2 | 3/2012 | Zhang et al. |
| 8,147,808 B2 | 4/2012 | Scavone et al. |
| 8,158,571 B2 | 4/2012 | Alonso et al. |
| 8,163,207 B2 | 4/2012 | Jung et al. |
| 8,192,838 B2 | 6/2012 | Goodson et al. |
| 8,206,820 B2 | 6/2012 | Bogaerts et al. |
| 8,246,869 B2 | 8/2012 | Stowell |
| 8,252,356 B2 | 8/2012 | Ogura et al. |
| 8,304,075 B2 | 11/2012 | Lang-Wittkowski et al. |
| 8,329,154 B2 | 12/2012 | Uchiyama et al. |
| 8,349,300 B2 | 1/2013 | Wells et al. |
| 8,354,369 B2 | 1/2013 | Beaussoubre et al. |
| 8,426,194 B2 | 4/2013 | Cao et al. |
| 8,460,791 B2 | 6/2013 | Hentze et al. |
| 8,460,864 B2 | 6/2013 | Cao et al. |
| 8,470,762 B2 | 6/2013 | Broze et al. |
| 2002/0016269 A1 | 2/2002 | Noda et al. |
| 2002/0102286 A1 | 8/2002 | Kantor et al. |
| 2002/0136773 A1 | 9/2002 | Scher et al. |
| 2002/0169233 A1 | 11/2002 | Schwantes |
| 2003/0017126 A1 | 1/2003 | Mahadeshwar et al. |
| 2003/0017959 A1 | 1/2003 | Baeck et al. |
| 2003/0024997 A1 | 2/2003 | Welch et al. |
| 2003/0031722 A1 | 2/2003 | Cao et al. |
| 2003/0077378 A1 | 4/2003 | Lou et al. |
| 2003/0108501 A1 | 6/2003 | Hofrichter et al. |
| 2003/0109391 A1 | 6/2003 | Midha et al. |
| 2003/0125222 A1 | 7/2003 | Jahns et al. |
| 2003/0139312 A1 | 7/2003 | Caswell et al. |
| 2003/0152542 A1 * | 8/2003 | Decoster et al. ........... 424/70.12 |
| 2003/0170304 A1 | 9/2003 | Devane et al. |

(56) References Cited

U.S. PATENT DOCUMENTS

| | | |
|---|---|---|
| 2003/0194416 A1 | 10/2003 | Shefer et al. |
| 2003/0199412 A1 | 10/2003 | Gupta et al. |
| 2003/0203978 A1 | 10/2003 | O'Brien et al. |
| 2003/0215417 A1 | 11/2003 | Uchiyama et al. |
| 2003/0216488 A1 | 11/2003 | Uchiyama et al. |
| 2003/0220220 A1 | 11/2003 | Bach et al. |
| 2004/0043078 A1 | 3/2004 | Herault |
| 2004/0071742 A1 | 4/2004 | Popplewell et al. |
| 2004/0091445 A1 | 5/2004 | Dykstra et al. |
| 2004/0101577 A1 | 5/2004 | Ahn et al. |
| 2004/0109920 A1 | 6/2004 | Reuscher et al. |
| 2004/0110898 A1 | 6/2004 | Dreja et al. |
| 2004/0137028 A1 | 7/2004 | de la Poterie |
| 2004/0138088 A1 | 7/2004 | Pereira et al. |
| 2004/0175347 A1 | 9/2004 | Bissett |
| 2004/0175404 A1 | 9/2004 | Shefer et al. |
| 2004/0197405 A1 | 10/2004 | Devane et al. |
| 2004/0208902 A1 | 10/2004 | Gupta |
| 2004/0214742 A1 | 10/2004 | Meli et al. |
| 2004/0220062 A1 | 11/2004 | Pereira et al. |
| 2004/0229769 A1 | 11/2004 | Smith et al. |
| 2005/0014674 A1 | 1/2005 | Liechty et al. |
| 2005/0038188 A1 | 2/2005 | Ahn et al. |
| 2005/0043209 A1 | 2/2005 | Schmiedel et al. |
| 2005/0048549 A1 | 3/2005 | Cao et al. |
| 2005/0112152 A1 | 5/2005 | Popplewell et al. |
| 2005/0113282 A1 | 5/2005 | Parekh et al. |
| 2005/0119351 A1 | 6/2005 | Van Der Schaaf et al. |
| 2005/0129759 A1 | 6/2005 | Sojka |
| 2005/0169793 A1 | 8/2005 | Wheatley et al. |
| 2005/0226900 A1 | 10/2005 | Winton Brooks et al. |
| 2005/0227907 A1 | 10/2005 | Lee et al. |
| 2005/0276831 A1 | 12/2005 | Dihora et al. |
| 2006/0008646 A1 | 1/2006 | Haggquist |
| 2006/0099168 A1 | 5/2006 | Corzani et al. |
| 2006/0116304 A1 | 6/2006 | McRitchie et al. |
| 2006/0127430 A1 | 6/2006 | Gupta |
| 2006/0134154 A1 | 6/2006 | Giles et al. |
| 2006/0160711 A1 | 7/2006 | Frank |
| 2006/0165740 A1 | 7/2006 | Frank |
| 2006/0166855 A1 | 7/2006 | Murad |
| 2006/0240105 A1 | 10/2006 | Devane et al. |
| 2006/0248665 A1 | 11/2006 | Pluyter et al. |
| 2006/0258557 A1 | 11/2006 | Popplewell et al. |
| 2006/0263311 A1 | 11/2006 | Scavone et al. |
| 2006/0263312 A1 | 11/2006 | Scavone et al. |
| 2006/0263313 A1 | 11/2006 | Scavone et al. |
| 2006/0263518 A1 | 11/2006 | Schwantes et al. |
| 2006/0263519 A1 | 11/2006 | Schwantes et al. |
| 2006/0263898 A1 | 11/2006 | Paget et al. |
| 2006/0275237 A1 | 12/2006 | Bissett et al. |
| 2006/0292098 A1 | 12/2006 | Scavone et al. |
| 2007/0020205 A1 | 1/2007 | Blin et al. |
| 2007/0031463 A1 | 2/2007 | Fotinos et al. |
| 2007/0041929 A1 | 2/2007 | Torgerson et al. |
| 2007/0048339 A1 | 3/2007 | Popplewell et al. |
| 2007/0071781 A1 | 3/2007 | Louys, Jr. et al. |
| 2007/0071978 A1 | 3/2007 | Sojka et al. |
| 2007/0078071 A1 | 4/2007 | Lee et al. |
| 2007/0122481 A1 | 5/2007 | Liversidge et al. |
| 2007/0123442 A1 | 5/2007 | Holzner et al. |
| 2007/0134411 A1 | 6/2007 | Cont et al. |
| 2007/0138671 A1 | 6/2007 | Anastasiou et al. |
| 2007/0138672 A1 | 6/2007 | Lee et al. |
| 2007/0138673 A1 | 6/2007 | Lee et al. |
| 2007/0138674 A1 | 6/2007 | Anastasiou et al. |
| 2007/0160561 A1 | 7/2007 | Ouali et al. |
| 2007/0160675 A1 | 7/2007 | Devane et al. |
| 2007/0173433 A1 | 7/2007 | Heibel et al. |
| 2007/0202063 A1 | 8/2007 | Dihora et al. |
| 2007/0207109 A1 | 9/2007 | Peffly et al. |
| 2007/0207174 A1 | 9/2007 | Pluyter et al. |
| 2007/0224274 A1 | 9/2007 | Siol |
| 2007/0248553 A1 | 10/2007 | Scavone et al. |
| 2007/0286837 A1 | 12/2007 | Torgerson et al. |
| 2007/0286904 A1 | 12/2007 | Popplewell et al. |
| 2007/0292361 A1 | 12/2007 | Virgallito et al. |
| 2007/0298061 A1 | 12/2007 | Boghani et al. |
| 2008/0008750 A1 | 1/2008 | Tochio et al. |
| 2008/0040082 A1 | 2/2008 | Stanton et al. |
| 2008/0057021 A1 | 3/2008 | Dykstra et al. |
| 2008/0102121 A1 | 5/2008 | Devane et al. |
| 2008/0107615 A1 | 5/2008 | Keene et al. |
| 2008/0113025 A1 | 5/2008 | Devane et al. |
| 2008/0118556 A1 | 5/2008 | Devane et al. |
| 2008/0128941 A1 | 6/2008 | Lopez et al. |
| 2008/0187596 A1 | 8/2008 | Dihora et al. |
| 2008/0199503 A1 | 8/2008 | Camargo et al. |
| 2008/0200359 A1 | 8/2008 | Smets et al. |
| 2008/0200363 A1 | 8/2008 | Smets et al. |
| 2008/0213451 A1 | 9/2008 | Ogura et al. |
| 2008/0226684 A1 | 9/2008 | Peppas |
| 2008/0311064 A1 | 12/2008 | Lei et al. |
| 2008/0317788 A1 | 12/2008 | Louzan Garcia et al. |
| 2009/0022764 A1 | 1/2009 | Frater et al. |
| 2009/0029900 A1 | 1/2009 | Cetti et al. |
| 2009/0035365 A1 | 2/2009 | Popplewell et al. |
| 2009/0047434 A1 | 2/2009 | Trophardy |
| 2009/0053165 A1 | 2/2009 | Brown et al. |
| 2009/0081265 A1 | 3/2009 | Peppas |
| 2009/0118399 A1 | 5/2009 | Benbakoura et al. |
| 2009/0149479 A1 | 6/2009 | Jenkins et al. |
| 2009/0202465 A1 | 8/2009 | Mougin et al. |
| 2009/0209661 A1 | 8/2009 | Somerville Roberts et al. |
| 2009/0221463 A1 | 9/2009 | Kitko et al. |
| 2009/0232857 A1 | 9/2009 | Peppas |
| 2009/0232858 A1 | 9/2009 | Peppas et al. |
| 2009/0247449 A1 | 10/2009 | Burdis et al. |
| 2009/0252789 A1 | 10/2009 | Trophardy |
| 2009/0258042 A1 | 10/2009 | Anastasiou et al. |
| 2009/0274905 A1 | 11/2009 | Schwantes |
| 2009/0275494 A1 | 11/2009 | Ferguson et al. |
| 2009/0289216 A1 | 11/2009 | Jung et al. |
| 2009/0324660 A1 | 12/2009 | Cetti et al. |
| 2010/0003518 A1 | 1/2010 | Grey |
| 2010/0061954 A1 | 3/2010 | Adams et al. |
| 2010/0068163 A1 | 3/2010 | Lu |
| 2010/0104611 A1 | 4/2010 | Chan et al. |
| 2010/0104612 A1 | 4/2010 | Cropper et al. |
| 2010/0104613 A1 | 4/2010 | Chan et al. |
| 2010/0119679 A1 | 5/2010 | Dihora et al. |
| 2010/0216684 A1 | 8/2010 | Ferguson et al. |
| 2010/0275384 A1 | 11/2010 | Broze et al. |
| 2010/0286018 A1 | 11/2010 | Hentze et al. |
| 2011/0003152 A1 | 1/2011 | Grey |
| 2011/0008427 A1 | 1/2011 | Biggs et al. |
| 2011/0008435 A1 | 1/2011 | Devane et al. |
| 2011/0020416 A1 | 1/2011 | Pluyter et al. |
| 2011/0033513 A1 | 2/2011 | Lei et al. |
| 2011/0093246 A1 | 4/2011 | Stanton et al. |
| 2011/0267702 A1 | 11/2011 | Fujimoto et al. |
| 2011/0268778 A1 | 11/2011 | Dihora et al. |
| 2011/0268802 A1 | 11/2011 | Dihora et al. |
| 2011/0269657 A1 | 11/2011 | Dihora et al. |
| 2011/0269658 A1 | 11/2011 | Dihora et al. |
| 2012/0010120 A1 | 1/2012 | Somerville Roberts et al. |
| 2012/0076839 A1 | 3/2012 | Chan et al. |
| 2012/0121677 A1 | 5/2012 | Franklin |
| 2012/0177924 A1 | 7/2012 | Jung et al. |
| 2012/0276175 A1 | 11/2012 | Dihora et al. |
| 2012/0276210 A1 | 11/2012 | Dihora et al. |
| 2012/0282309 A1 | 11/2012 | Dihora et al. |
| 2012/0322709 A1 | 12/2012 | Li et al. |
| 2013/0137625 A1 | 5/2013 | Stowell |

FOREIGN PATENT DOCUMENTS

| | | |
|---|---|---|
| DE | 10062585 A1 | 6/2002 |
| DE | 102005029777 | 1/2007 |
| DE | 102006058253 | 6/2008 |
| DE | 102008044700 | 2/2010 |
| EP | 0303461 A1 | 2/1989 |
| EP | 0462709 A2 | 12/1991 |
| EP | 0510761 A1 | 10/1992 |

(56) References Cited

FOREIGN PATENT DOCUMENTS

| | | |
|---|---|---|
| EP | 0523287 A1 | 1/1993 |
| EP | 0290223 B1 | 12/1994 |
| EP | 0820762 A1 | 1/1998 |
| EP | 0829259 A1 | 3/1998 |
| EP | 0535942 B1 | 2/1999 |
| EP | 1034705 | 9/2000 |
| EP | 1201743 A1 | 5/2002 |
| EP | 1243318 | 9/2002 |
| EP | 1243320 | 9/2002 |
| EP | 1247568 | 10/2002 |
| EP | 1024785 B1 | 1/2003 |
| EP | 1030734 B1 | 8/2003 |
| EP | 1023041 B1 | 1/2005 |
| EP | 1502646 A1 | 2/2005 |
| EP | 1637188 | 3/2006 |
| EP | 1702674 | 9/2006 |
| EP | 1850887 | 11/2007 |
| EP | 1600151 B1 | 8/2008 |
| EP | 2090284 | 8/2009 |
| EP | 2132294 | 12/2009 |
| FR | 2702961 | 9/1994 |
| FR | 2881048 | 7/2006 |
| GB | 1451411 | 10/1976 |
| GB | 1478788 | 7/1977 |
| GB | 1546480 | 5/1979 |
| GB | 2062570 | 5/1981 |
| GB | 2217603 A | 1/1989 |
| GB | 2334724 A | 1/1999 |
| JP | 54-5051 | 1/1979 |
| JP | 58-19261 | 2/1983 |
| JP | 59-139268 | 8/1984 |
| JP | 61-244366 | 10/1986 |
| JP | 62116506 | 5/1987 |
| JP | 01-256965 | 10/1989 |
| JP | 02-036803 | 2/1990 |
| JP | 02-052661 | 2/1990 |
| JP | 04-021513 | 1/1992 |
| JP | 04-082558 | 3/1992 |
| JP | 04-156851 | 5/1992 |
| JP | 05-017338 | 1/1993 |
| JP | 06-000361 | 1/1994 |
| JP | 06-041576 U | 6/1994 |
| JP | 07-075666 | 3/1995 |
| JP | 07-305049 | 11/1995 |
| JP | 10195478 A | 7/1998 |
| JP | 10231119 | 9/1998 |
| JP | 2001049287 | 2/2001 |
| JP | 2002326904 | 11/2002 |
| JP | 2003099986 A | 4/2003 |
| JP | 2003161893 | 6/2003 |
| JP | 2004099743 | 4/2004 |
| JP | 2005194308 | 7/2005 |
| JP | 2008156565 | 7/2008 |
| JP | 2009035454 | 2/2009 |
| JP | 2009290236 | 12/2009 |
| KR | 20090082704 | 9/2010 |
| WO | 84/03630 A1 | 9/1984 |
| WO | 92/20771 | 11/1992 |
| WO | 93/08600 A1 | 4/1993 |
| WO | 97/47720 A2 | 12/1997 |
| WO | 98/12298 A2 | 3/1998 |
| WO | 98/26808 A2 | 6/1998 |
| WO | 00/32601 | 6/2000 |
| WO | 00/41528 | 7/2000 |
| WO | 00-65020 | 11/2000 |
| WO | 00/67718 A1 | 11/2000 |
| WO | 01/41915 | 6/2001 |
| WO | 01/41915 A1 | 6/2001 |
| WO | 01/74310 A2 | 10/2001 |
| WO | 03/002248 A1 | 1/2003 |
| WO | 03/020867 A1 | 3/2003 |
| WO | 2004/006967 A1 | 1/2004 |
| WO | 2004/060418 A1 | 7/2004 |
| WO | 2004/096895 A1 | 11/2004 |
| WO | 2005/041908 A1 | 5/2005 |
| WO | 2005/047232 A1 | 5/2005 |
| WO | 2005/55990 A1 | 6/2005 |
| WO | 2006/027664 A2 | 3/2006 |
| WO | 2006/127454 A2 | 11/2006 |
| WO | 2007/040517 | 4/2007 |
| WO | 2007/128326 A1 | 11/2007 |
| WO | 2007/137441 A1 | 12/2007 |
| WO | 2008/005693 A2 | 1/2008 |
| WO | 2008/058868 | 5/2008 |
| WO | 2008/129028 A1 | 10/2008 |
| WO | 2008/145874 A1 | 12/2008 |
| WO | 2009/047127 A1 | 4/2009 |
| WO | 2009/047745 A2 | 4/2009 |
| WO | 2009/080695 A1 | 7/2009 |
| WO | 2009/083941 A2 | 7/2009 |
| WO | 2009/093812 A1 | 7/2009 |
| WO | 2009/106318 A2 | 9/2009 |
| WO | 2009/134234 A1 | 11/2009 |
| WO | 2010/079466 A2 | 7/2010 |
| WO | WO 2010079466 A2 * | 7/2010 |

OTHER PUBLICATIONS

International Search Report for PCT/IB2010/052120 mailed Dec. 29, 2010, 4 pages.

Huber et al.—"Capsular Adhesives", TAPPI, vol. 49, No. 5, pp. 41A-44A, May 1966.

Leo, Albert J., et al.—Methods of Calculating Partition Coefficients, Comprehensive Medicinal Chemistry, vol. 4, p. 295, 1990.

Zhang, Z., et al.—"Mechanical Properties of Melamine-Formaldehyde Microcapsules", J. Microencapsulation, vol. 18, No. 5, pp. 593-602, 2001.

Brunauer, et al.—"Absorption of Gases in Multimolecular Layers"—Journal of the American Chemical Society, vol. 60, pp. 309-319, 1938.

Washburn, E.W.—"The Dynamics of Capillary Flow"—Phys. Rev., 17 374-375, 1921.

Fowkes, F.M.—"Attractive Forces at Interfaces"—Industrial and Engineering Chemistry, vol. 56, No. 12, pp. 40-52, 1964.

Good, R.J., et al.—A Theory for Estimation of Surface and Interfacial Energies, III, Estimation of Surface Energies or Solids from Contact Angle Data, L.A.; Journal of Phys. Chem., vol. 64, pp. 561-565, 1960.

Zim's Crack Creme (R), 2003, Perfecta Products, Inc., Berlin Center, Ohio 44401.

U.S. Appl. No. 14/032,835, filed Sep. 20, 2013, Dihora et al.
U.S. Appl. No. 14/032,859, filed Sep. 20, 2013, Dihora et al.
U.S. Appl. No. 14/032,868, filed Sep. 20, 2013, Cetti et al.
U.S. Appl. No. 14/032,888, filed Sep. 20, 2013, Li et al.
U.S. Appl. No. 14/045,661, filed Oct. 3, 2013, Dihora et al.
U.S. Appl. No. 14/045,670, filed Oct. 3, 2013, Dihora et al.

Herbig—Microencapsulation, Kirk-Othmer Encyclopedia of Chemical Technology, vol. 13, Second completely revised edition, Jan. 1, 1967, pp. 436-456.

* cited by examiner

CONDITIONER COMPOSITIONS WITH INCREASED DEPOSITION OF POLYACRYLATE MICROCAPSULES

CROSS REFERENCE TO RELATED APPLICATION

This application claims the benefit of U.S. Provisional Application Ser. No. 61/472,860 filed Apr. 7, 2011.

FIELD OF THE INVENTION

The present invention relates to conditioner compositions containing polyacrylate microcapsules, wherein the polyacrylate microcapsules have increased deposition onto hair.

BACKGROUND OF THE INVENTION

Many of the conditioner products in the market today work to deliver benefits to hair by depositing benefit agents such as perfumes and conditioning agents onto the hair during conditioning. As a result, there is a desire to maximize the effectiveness of such benefit agents by increasing their delivery and retention onto hair. One method of achieving this objective is to encapsulate such benefit agents in microcapsules. While these microcapsules are able to encapsulate a wide variety of benefit agents and deliver them to hair, it is still difficult to improve the retention and delivery efficiencies of such benefit agents. Such agents may be lost due to the agents' physical or chemical characteristics, may be washed off of the hair during conditioning, or may be incompatible with other compositional components already on the hair. Consumers today desire conditioning compositions that deposit and retain encapsulated benefit agents onto hair even after an extended period of time.

One known method for improving the deposition of microcapsules onto hair during treatment involves the use of certain cationic deposition polymers. However, this alone does not necessarily ensure adequate deposition of microcapsules onto hair.

Accordingly, there is a need for a conditioner composition that provides an increased deposition of encapsulated benefit agents onto hair. In addition, there is a need for a polymer system that associates with microcapsule surfaces, and that when sheared, allows the encapsulated benefit agents to be released. Furthermore, there is a need for a conditioner composition that provides an increased retention of encapsulated benefit agents onto the hair for an extended period of time.

SUMMARY OF THE INVENTION

A conditioner composition comprising: from about 0.001% to about 10% of an anionic charged polyacrylate microcapsule; from about 0.01% to about 2% of a deposition aid selected from the group consisting of cationic deposition polymer, aminosilicone, and combinations thereof; from about 2% to about 25% of a conditioner agent; and a carrier.

A method of making a conditioner composition, wherein the composition is formed by a process comprising the steps of: coating a polyacrylate microcapsule with an anionic emulsifier to form an anionic polyacrylate microcapsule; combining the anionic polyacrylate microcapsule with a deposition aid to form a premix; adding the premix to a conditioner agent and a carrier.

A method of making a conditioner composition, wherein the composition is formed by a process comprising the steps of: coating a polyacrylate microcapsule with an anionic emulsifier to form an anionic polyacrylate microcapsule; combining the anionic polyacrylate microcapsule with a deposition aid to form a premix; adding the premix to an anionic surfactant; adding the resulting composition of step (c) to a conditioner agent and a carrier.

DETAILED DESCRIPTION OF THE INVENTION

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Definitions

As used herein "consumer product" means conditioner products intended to be used or consumed in the form in which it is sold. Such products include but are not limited to products for and/or methods relating to treating hair including conditioning.

As used herein, the term "personal care composition" includes, unless otherwise indicated, any personal care composition that can be applied to the keratinaceous surfaces of the body including the skin and/or hair.

As used herein, the term "conditioning agent" includes cationic surfactant, high melting point fatty compound, a silicone compound, and mixtures thereof.

As used herein, the term "deposition aid" includes cationic deposition polymer, aminosilicone, and combinations thereof.

As used herein, the term "fluid" includes liquids and gels.

As used herein, the terms "microcapsule," "encapsulated benefit agents," and "solid particulates," refers to polyacrylate microcapsules.

As used herein, the term "premix" refers to the combination of anionic polyacrylate microcapsules with cationic deposition polymers or aminosilicones.

As used herein, the terms "include," "includes," and "including," are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Benefits of Anionic Polyacrylate Microcapsules

Consumers desire conditioner compositions that deposit and retain encapsulated benefit agents onto their hair during the conditioning process. Traditionally, a variety of approaches have been employed to improve deposition of microcapsules, including (1) using specific block copolymers to covalently bind to the microcapsules, and (2) using cationic water soluble polymers to coat the microcapsules in order to increase the affinity of the microcapsules to the substrate of interest. However, it is desired to have improved deposition over the traditional approaches.

It has been surprisingly found that a synergy exists between anionic emulsifiers and polyacrylate microcapsules, resulting in anionic polyacrylate microcapsules. When such anionic microcapsules are mixed with a deposition aid, microstructures are formed at the surface of the anionic polyacrylate. Such anionic microstructures display high viscoelasticity, remain in tact even upon dilution during cleansing, and display strong adhesion to keratinaceous hair surfaces. Combined with conditioning compositions, these properties result in improved delivery efficiency of the encapsulated benefit agents to hair.

It is believed that the conditioner composition comprising anionic polyacrylate microcapsules, along with a deposition aid such as a cationic deposition polymer or an aminosilicone, delivers a higher deposition rate than conditioner compositions containing non-anionic polyacrylates. In addition, anionic polyacrylate microcapsules with specific cationic deposition polymers or with aminosilicones also have a higher retention rate on the hair even over an extended period of time. Applicants surprising discovery of adding anionic emulsifier to microcapsules to form anionic microcapsules can be accomplished by either: (1) adding the anionic emulsifier to an already formed microcapsule or (2) allowing the anionic emulsifier to associate with the microcapsule surface during the microcapsule making process. Once formed, the anionic polyacrylate microcapsules are combined with the specific cationic polymer(s) chosen or the specific aminosilicone chosen to form a premix for addition to a surfactant containing conditioner composition.

Anionic Emulsifier

The addition of an anionic emulsifier forms a microstructure with a specified cationic deposition polymer or with an aminosilicone at the external surface of the microcapsules, i.e., the anionic emulsifier is at least a part of the external surface of the microcapsules, or is physically or chemically bound to the external surface of the microcapsules. Such physical bindings include, for example, hydrogen bonding, ionic interactions, hydrophobic interactions, and electron transfer interactions. Such chemical bindings include, for example, covalent bindings such as covalent grafting and crosslinking.

The anionic emulsifier is present at a level by weight of from about 0.1% to about 40%, from about 0.5% to about 10%, or from about 0.5% to about 5%, by weight of the polyacrylate microcapsule.

A variety of anionic emulsifiers can be used in the conditioner compositions of the present invention as described below. The anionic emulsifiers include, by way of illustrating and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

In addition, it is desirable to use anionic emulsifiers that have acrylate functionality since these can be covalently linked to the shell portion of the polyacrylate microcapsules during the microcapsule making process. Anionic emulsifiers useful herein include, but aren't limited to: Poly(meth)acrylic acid; copolymers of (meth)acrylic acids and its (meth)acrylates with C1-22 alkyl, C1-C8 alkyl, butyl; copolymers of (meth)acrylic acids and (meth)acrylamide; Carboxyvinylpolymer; acrylate copolymers such as Acrylate/C10-30 alkyl acrylate crosspolymer, Acrylic acid/vinyl ester copolymer/Acrylates/Vinyl Isodecanoate crosspolymer, Acrylates/Palmeth-25 Acrylate copolymer, Acrylate/Steareth-20 Itaconate copolymer, and Acrylate/Celeth-20 Itaconate copolymer; Polystyrene sulphonate, copolymers of methacrylic acid and acrylamidomethylpropane sulfonic acid, and copolymers of acrylic acid and acrylamidomethylpropane sulfonic acid; carboxymethycellulose; carboxy guar; copolymers of ethylene and maleic acid; and acrylate silicone polymer. Neutralizing agents may be included to neutralize the anionic emulsifiers herein. Non-limiting examples of such neutralizing agents include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof. Commercially available anionic emulsifiers include, for example, Carbomer supplied from Noveon under the tradename Carbopol 981 and Carbopol 980; Acrylates/C10-30 Alkyl Acrylate Crosspolymer having tradenames Pemulen TR-1, Pemulen TR-2, Carbopol 1342, Carbopol 1382, and Carbopol ETD 2020, all available from Noveon; sodium carboxymethylcellulose supplied from Hercules as CMC series; and Acrylate copolymer having a tradename Capigel supplied from Seppic. In another embodiment, anionic emulsifiers are carboxymethylcelluloses.

Polyacrylate Microcapsules

Various processes for microencapsulation, and exemplary methods and materials, are set forth in U.S. Pat. Nos. 6,592,990; 2,730,456; 2,800,457; 2,800,458; and 4,552,811. Each patent described throughout this application is incorporated herein by reference to the extent each provides guidance regarding microencapsulation processes and materials.

The present invention teaches a low permeability microcapsule comprising a core material and a wall material at least partially surrounding, and in another embodiment, completely surrounding, a core material. In the present invention, the polyacrylate microcapsules are benefit agent microcapsule particulates which encapsulate benefit agents by capsule wall materials comprised of polymers.

Capsule wall materials useful herein include, for example, those formed from melamine-formaldehyde or urea-formaldehyde condensates, melamine-resorcinol or urea-resorcinol condensates, as well as similar types of aminoplasts, gelatin, polyurethane, polyamide, polyolefin, polysaccaharide, protein, silicone, lipid, modified cellulose, gums, polyacrylate, polyphosphate, polystyrene, and polyesters, or combinations of these materials. In another embodiment, a wall material that provides low permeability is polyacrylate.

The benefit agents of the core may comprise a material selected from the group consisting of perfumes; brighteners; enzymes; perfumes; conditioning agents, thickeners; antimicrobial agents; sensates in one aspect a cooling agent; attractants, in one aspect a pheromone; dyes; pigments; bleaches; and mixtures thereof.

The polyacrylate microcapsules useful herein are those releasing the benefit agents for a period of time after initial application. Potential trigger mechanisms for release of the encapsulated benefit agents may include, but are not limited to, mechanical forces, dehydration, light, pH, temperature, or even changes in ionic strength.

Process of Making Anionic Polyacrylate Microcapsules

An anionic polyacrylate microcapsule can be formed by either: (1) coating an already formed microcapsule with an anionic emulsifier; or (2) adding the anionic emulsifier to the microcapsule during the microcapsule making process. Any known method for generating a microcapsule is useful herein. Example methods for making polyacrylate microcapsules are disclosed in U.S. Patent Application 61/328,949; U.S. Patent Application 61/328,954; U.S. Patent Application 61/328,962; and U.S. Patent Application 61/328,967.

In one embodiment, polyacrlyate microcapsules are formed from water in oil, or oil in water emulsifications. During the polyacrylate microcapsule making process, a first composition is prepared as an oil phase. The oil phase may comprise oil; an oil soluble or dispersible primary, secondary, or tertiary amine; a multifunctional acrylate or methacrylate monomer or oligomer; an oil soluble acid; an initiator, and combinations thereof. In one embodiment, a nitrogen blanket is employed while the solution is mixed. Gradually, the temperature is increased to create a first composition reaction product. After the first composition reaction product is formed, a second composition is added to the reaction product.

The second composition is prepared as a water phase. The water phase may comprise water; an emulsifier that may be water soluble or water dispersible polymer or copolymer; at least one water phase initiator; one or more of an alkali or alkali salt, and combinations thereof. By water phase initiator, it is meant that the initiator is soluble or dispersible in water.

The second composition is then added to the oil solution of the first composition reaction product. This addition creates an oil-in-water emulsion. The reaction of the first composition in the presence of the second composition results in the formation of a low permeability microcapsule wall. The emulsion is further heated for a time and temperature sufficient to decompose the free radicals which are present in either one or both of the oil and water phases.

Furthermore, the polymerization of the monomers and oligomers in the oil phase causes a precipitation of the polymerized material. The precipitation of microcapsule wall material forms at the interface of the water and oil phases The anionic polyacrylate microcapsule is contained in the composition at a level by weight of from about 0.01% to about 50%, from about 0.05% to about 10%, from about 0.1% to about 8%, or from about 0.25% to 3%.

The anionic polyacrylate microcapsules useful herein are those having a particle size of from about 1 micron to about 80 microns, from about 2 microns to about 50 microns, and from about 5 microns to about 30 microns.

A. Coating a Microcapsule

In one embodiment of the invention, the anionic emulsifier is added to an already formed polyacrylate microcapsule. The anionic emulsifier attaches to the surface of the microcapsule through hydrogen bonding, van der Waals forces, ionic interactions, hydrophobic interactions, or chemical reactions. In one aspect, the anionic emulsifier surrounds at least a part of the external surface of the polyacrylate microcapsule, or is physically or chemically bound to the external surface of the polyacrylate microcapsule.

B. Adding Anionic Emulsifier to a Microcapsule

In another embodiment, the anionic emulsifier associates with the microcapsule surface during the microcapsule making process. When making the microcapsule, the anionic emulsifier is solubilized in an aqueous phase, which may optionally contain a free radical initiator, prior to emulsification of the oil. The excess aqueous phase is then added to the oil phase to form an oil-in-water emulsion. The emulsion is then heated for a time and at a temperature sufficient to decompose the free radicals which are positioned in one or both of the oil and aqueous phases. Microcapsule wall material is thereby formed at the interface of the water and oil phases. In one embodiment, when the emulsifier is comprised of acrylate moieties, the emulsifier may become chemically bound to the interfacial wall material.

C. Forming a Premix

Once the anionic polyacrlyate microcapsule is formed by either formation step, the anionic polyacrylate microcapsule is added to a deposition aid to form a premix. It has been surprisingly found that the anionic charge on the polyacrylate microcapsule leads to the formation of a microstructure on the shell of the microcapsule when combined with a deposition aid in the premix. This premix exhibits anionic polyacrylate microcapsules that have a higher viscoelasticity to the hair than microcapsules without an anionic charge and specific deposition aid thus giving a benefit to the hair.

Slurry/Aggolmerate

In one embodiment, the anionic polyacrylate microcapsules are contained in a slurry. The slurry may be combined with an adjunct ingredient to form a composition, for example, a conditioning consumer product.

In one aspect, the slurry may comprise one or more processing aids, selected from the group consisting of water, aggregate inhibiting materials such as divalent salts; particle suspending polymers such as xanthan gum, guar gum, and caboxy methyl cellulose. In another embodiment, said processing aids may be selected from the group consisting of amphoteric surfactants such as cocamidopropyl betaine (CAPB), zwitterionic surfactants, cationic swellable polymers, latex particles such as acrylic based ester Rheovis CDE, and mixtures thereof.

In one aspect, the slurry may comprise a carrier selected from the group consisting of polar solvents, including but not limited to, water, ethylene glycol, propylene glycol, polyethylene glycol, glycerol; nonpolar solvents, including but not limited to, mineral oil, perfume raw materials, silicone oils, hydrocarbon paraffin oils, and mixtures thereof.

In another embodiment, the anionic polyacrylate microcapsules are contained in an agglomerate with a second material. In one aspect, said second materials may comprise a material selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

Cationic Deposition Polymer

In one embodiment, the deposition aid for use in the conditioner composition of the present invention comprises a cationic deposition polymer that forms a premix when added to the anionic polyacrylate microcapsules. Any known natural or synthetic cationic deposition polymer can be used herein. Examples include those polymers disclosed in U.S. Pat. No. 6,649,155; U.S. patent application Ser. No. 12/103, 902; U.S. Patent Publication 2008/0206355; and U.S. Patent Publication No. 2006/0099167A1.

The cationic deposition polymer is included in the composition at a level from about 0.01% to about 2%, in one embodiment from about 1.5% to about 1.9%, in another embodiment from about 1.8% to about 2.0%, in view of providing the benefits of the present invention.

The cationic deposition polymer is a water soluble polymer with a charge density from about 0.5 milliequivalents per gram to about 12 milliequivalents per gram. The cationic deposition polymer used in the composition has a molecular weight of about 100,000 Daltons to about 5,000,000 Daltons. The cationic deposition polymer is a low charge density cationic polymer.

In one embodiment, the cationic deposition polymer is a synthetic cationic deposition polymer. A variety of synthetic cationic deposition polymers can be used including mono- and di-alkyl chain cationic surfactants. In one embodiment, mono-alkyl chain cationic surfactants are chosen including, for example, mono-alkyl quaternary ammonium salts and mono-alkyl amines. In another embodiment, di-alkyl chain cationic surfactants are used and include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

In another embodiment, the cationic deposition polymer is a naturally derived cationic polymer. The term, "naturally derived cationic polymer" as used herein, refers to cationic deposition polymers which are obtained from natural sources. The natural sources may be polysaccharide polymers. Therefore, the naturally derived cationic polymer may be selected from the group comprising starches, guar, cellulose, cassia, locust bean, Konjac, Tara, galactomannan, tapioca, and synthetic polymers. In a further embodiment, cationic deposition polymers are selected from Mirapol 100S (Rhodia), Jaguar C17, Tapioca starch (Akzo), and polyTriquat.

Aminosilicone

In another embodiment, the deposition aid for use in the conditioner composition of the present invention comprises an aminosilicone that forms a premix when added to the anionic polyacrylate microcapsules. The aminosilicone is contained in the composition at a level by weight of from about 0.1% to about 15%, from about 0.3% to about 10%, from about 0.6% to about 5%, or from about 0.8% to about 2.5% in order to provide increased deposition of the microcapsules. The level of aminosilicone in the premix is relevant since too much aminosilicone causes a sticky feeling to the hair and/or hands of the consumer. In addition, too much aminosilicone may not provide enhanced and/or prolonged benefits from the benefit agent microcapsules due to an accumulation of coating on the capsule wall. This accumulation of aminosilicone in turn prevents the capsule wall from breaking and releasing the benefit agents.

In one embodiment, the aminosilicones useful herein are water-insoluble. In the present invention, "water-insoluble aminosilicone" means that the aminosilicone has a solubility of 10 g or less per 100 g water at 25° C., in another embodiment 5 g or less per 100 g water at 25° C., and in another embodiment 1 g or less per 100 g water at 25° C. In the present invention, "water-insoluble aminosilicone" means that the aminosilicone is substantially free of copolyol groups. If copolyol groups are present, they are present at a level of less than 10%, less than 1%, or less than 0.1% by weight of the amionosilicone.

The aminosilicones useful herein are those having an amine content of from about 0.04 to about 0.3 m mol/g, from about 0.07 to about 0.25 m mol/g, or from about 0.1 to about 0.2 m mol/g in order to balance deposition enhancing benefits and usage feel.

In one embodiment, the aminosilicones have a tertiary or quaternary amine. Such amine sites can attach to at least one of the terminal ends of a silicone backbone and/or can attach to the silicone backbone as grafted side chains. In the present invention, aminosilicones have the amine sites attaching to the silicone backbone as grafted side chains.

Such water-insoluble aminosilicones useful herein include, but are not limited to, those having the following structure:

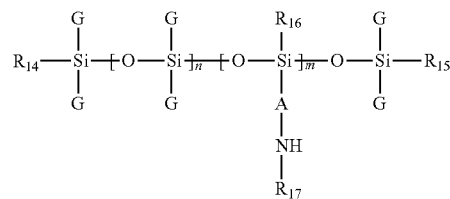

wherein:
a sum (n+m) ranges from about 2 to about 2000, in another embodiment from about 150 to about 2000, in another embodiment from about 250 to about 1200, and in another embodiment from about 300 to about 800;
n is a number ranging from about 1 to about 1999, and m is a number ranging from about 1 to about 1999; and n and m are chosen such that a ratio of m:n is from about 1:1000 to about 1:10, in another embodiment from about 1:1000 to about 1:25, in another embodiment from about 1:800 to about 1:50, in another embodiment from about 1:500 to about 1:50, and in another embodiment from about 1:400 to about 1:100;
$R_{14}$, $R_{15}$, $R_{16}$, which may be identical or different, are chosen from a hydroxyl radical, C1-C4 alkoxy radicals and methyl, $R_{14}$ and $R_{15}$ are hydroxyl radical and/or C1-C4 alkoxy radicals and $R_{16}$ is methyl;
A is chosen from linear and branched C3-C8 alkenyl radicals;
$R_{17}$ is chosen from H, phenyl, linear or branched C1-C4 alkyl radical, benzyl or linear or branched (C2-C8)$NH_2$; and
G is chosen from H, phenyl, hydroxyl, C1-C8 alkyl, methyl.
These aminosilicones may be of the random or block type.

Suitable aminosilicones of the present invention include, but are not limited to, organo-modified silicones with amine functionality which are available commercially under the trade names ADM1100 and ADM1600 from Wacker Silicones, AP6087, DC2-8211, DC8822, DC8822A, DC8803, DC2-8040, DC2-8813, DC2-8630 and DC8566 from Dow Corning Corporation, KF-862, KF-861, KF-8625, KF-8005, KF-8004, KF-8675, KF-873, and X-52-2328 from Shin-Etsu Corporation, and TSF 4702, TSF 4703, TSF 4704, TSF 4705, TSF 4707, TSF 4708, TSF 4709, F42-B3115, SF 1708, SF 1923, SF 1921, SF 1925, OF TP AC3309, OF 7747, OF-NH TP AI3631, OF-NH TP AI3683 from GE Bayer Silicones.

Aminosilicones useful herein are those with viscosities from about 1,000 mPa·s to 400,000 mPa·s, or from about 2,000 mPa·s to about 100,000 mPa·s, or from about 3,000 mPa·s to about 20,000 mPa·s, or from about 4,000 mPa·s to about 10,000 mPa·s. The specific viscosity levels provide conditioning efficiency, incorporation processing, and spreadability of the conditioner on the hair of the consumer.

The aminosilicones useful herein can be used as a single compound, or as a blend or mixture with other silicone compounds and/or solvents.

In one embodiment, the aminosilicone is incorporated in the present composition in the form of an emulsion. The emulsion is made by mechanical mixing or emulsion polymerization. Emulsion polymerization can be done with or without the aid of a surfactant. If a surfactant is included, the surfactant is selected from anionic surfactants, nonionic surfactants, cationic surfactants, and mixtures thereof.

Forming a Premix

In one embodiment, the cationic deposition polymer and the anionic polyacrylate microcapsule are mixed to form a premix before addition to the conditioner composition comprising a cationic surfactant and a carrier. In another embodiment, the aminosilicone and the anionic polyacrylate microcapsule are mixed to form a premix before addition to the conditioner composition comprising a cationic surfactant and a carrier.

The weight ratio of the anionic polyacrylate microcapsule to either the cationic deposition polymer or the aminosilicone (based on the dry weight of the anionic microcapsules and the dry weight of the cationic deposition polymer and the aminosilicone) is from about 0.5:30 to about 20:1, from about 5:15 to about 15:1, and from about 5:1 to about 12:1. It is believed that too much cationic polymer or aminosilicone may not provide enhanced and/or prolonged benefits to the benefit agent microcapsules due to the formation of excess coating on the capsule wall. This excess coating may prevent the microcapsule wall from breaking and releasing the benefit agents.

Microcapsules and anionic emulsifiers may be dispersed in solvents such as water while mixing with the cationic deposition polymer. In one embodiment, the amount of water present is from about 90% to about 50%, in another embodiment from about 70% to about 50%, and in another embodiment from about 60% to about 50%. In one embodiment of the invention, the anionic emulsifiers associate with the microcapsule walls to form anionic polyacrylate microcapsules prior to their mixing with cationic deposition polymers.

Conditioning Agent and Carrier

Particles made according to the invention can be employed in compositions which include both a conditioning agent and a carrier. The resulting conditioning compositions have an oil phase and an aqueous phase. The polyacrylate microcapsules reside in the aqueous phase of such conditioning compositions.

The conditioning agent may contain the following components:

A. Cationic Surfactant

The conditioning agent for use in the conditioner composition of the present invention may contain a cationic surfactant. Any known cationic surfactant may be used herein. Examples include those surfactants disclosed in U.S. Patent (2009/0143267A1). Concentrations of cationic surfactant in the composition typically range from about 0.05% to about 3%, in another embodiment from about 0.075% to about 2.0%, and in yet another embodiment from about 0.1% to about 1.0

A variety of cationic surfactants including mono- and di-alkyl chain cationic surfactants can be used in the conditioner composition of the present invention. In one embodiment, mono-alkyl chain cationic surfactants are used in order to provide a consumer desired gel matrix and wet conditioning benefits. Such mono-alkyl cationic surfactants include, for example, mono-alkyl quaternary ammonium salts and mono-alkyl amines.

In another embodiment, cationic surfactants such as di-alkyl chain cationic surfactants are used in combination with mono-alkyl chain cationic surfactants. Such di-alkyl chain cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Cationic surfactants can also be a salt of a mono-long alkyl quaternized ammonium and an anion, wherein the anion is selected from the group consisting of halides such as chloride and bromide, C1-C4 alkyl sulfate such as methosulfate and ethosulfate, and mixtures thereof. In one embodiment, the anion is selected from the group consisting of halides such as chloride.

The mono-long alkyl quaternized ammonium salts useful herein are those having the formula (I):

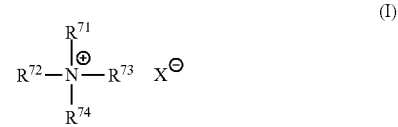

wherein one of $R^{71}$, $R^{72}$, $R^{73}$ and $R^{74}$ is selected from an aliphatic group of from 16 to 40 carbon atoms or an aromatic, alkoxy, polyoxyalkylene, alkylamido, hydroxyalkyl, aryl or alkylaryl group having up to about 40 carbon atoms; the remainder of $R^{71}$, $R^{72}$, $R^{73}$ and $R^{74}$ are independently selected from an aliphatic group of from 1 to about 8 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as metho sulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. In one embodiment, one of $R^{71}$, $R^{72}$, $R^{73}$ and $R^{74}$ is selected from an alkyl group of from 16 to 40 carbon atoms, in another embodiment from 18 to 26 carbon atoms, and in another embodiment from 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Such mono-long alkyl quaternized ammonium salts provides an improved slippery feel to wet hair when compared to the slippery feeling produced by multi-long alkyl quaternized ammonium salts. In addition, mono-long alkyl quaternized ammonium salts provide improved hydrophobicity of the hair and give a smooth feel to dry hair, compared to amine or amine salt cationic surfactants.

In one embodiment, cationic surfactants are those having a longer alkyl group, i.e., C18-22 alkyl group. Such cationic surfactants include, for example, behenyl trimethyl ammonium chloride, methyl sulfate or ethyl sulfate, and stearyl trimethyl ammonium chloride, methyl sulfate or ethyl sulfate. In another embodiment, the cationic surfactants are behenyl trimethyl ammonium chloride, methyl sulfate or ethyl sulfate. In another embodiment, the cationic surfactants are behenyl trimethyl ammonium chloride. Cationic surfactants having a longer alkyl group provide improved deposition of microcapsules onto the hair thereby providing an increased amount of benefit agents on the hair. In addition, cationic surfactants having a longer alkyl group provide reduced irritation to the skin of the consumer compared to cationic surfactants having a shorter alkyl group.

Mono-alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; in another embodiment l-glutamic acid, lactic acid, citric acid. In one embodiment, the amines herein are partially neutralized with any of the acids at a molar ratio of the amine to the acid of from about 1:0.3 to about 1:2, or from about 1:0.4 to about 1:1.

B. High Melting Point Fatty Compound

The conditioner agent for use in the conditioner composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section.

Among a variety of high melting point fatty compounds, fatty alcohols are used in one aspect the present invention. The fatty alcohols useful herein are those having from about 14 to about 30 carbon atoms, or even from about 16 to about 22 carbon atoms. These fatty alcohols are saturated and can be straight or branched chain alcohols. In one aspect, fatty alcohols include, for example, cetyl alcohol, stearyl alcohol, behenyl alcohol, and mixtures thereof.

In one embodiment, high melting point fatty compounds of a single compound of high purity are used. Single compounds of pure fatty alcohols are selected from the group consisting of pure cetyl alcohol, stearyl alcohol, and behenyl alcohol. By "pure" herein, what is meant is that the compound has a purity of at least about 90%, or even at least about 95%. These single compounds of high purity provide good rinsability from the hair when the consumer rinses off the composition.

The high melting point fatty compound is included in the composition at a level of from about 0.1% to about 40%, from about 1% to about 30%, from about 1.5% to about 16% by weight of the composition, or even from about 1.5% to about 8% in view of providing improved conditioning benefits such as slippery feel during the application to wet hair, softness and moisturized feel on dry hair.

D. Nonionic Polymers

The conditioner agent for use in the conditioner composition of the present invention may include a nonionic polymer. Polyalkylene glycols having a molecular weight of more than about 1000 are useful herein. Useful are those having the following general formula:

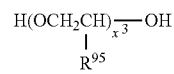

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

E. Silicone Compound

The conditioner agent for use in the conditioner composition may include a silicone compound.

1. Silicones

The silicone compound may comprise volatile silicone, non-volatile silicones, or combinations thereof. In one aspect, non-volatile silicones are employed. If volatile silicones are present, it will typically be incidental to their use as a solvent or carrier for commercially available forms of non-volatile silicone materials ingredients, such as silicone gums and resins. The silicone compounds may comprise a silicone fluid conditioning agent and may also comprise other ingredients, such as a silicone resin to improve silicone fluid deposition efficiency or enhance glossiness of the hair.

The concentration of the silicone compound typically ranges from about 0.01% to about 10%, from about 0.1% to about 8%, from about 0.1% to about 5%, or even from about 0.2% to about 3%. Non-limiting examples of suitable silicone compounds, and optional suspending agents for the silicone, are described in U.S. Reissue Pat. Nos. 34,584, U.S. Pat. Nos. 5,104,646, and 5,106,609. The silicone compounds for use in the compositions of the present invention typically have a viscosity, as measured at 25° C., from about 20 centistokes to about 2,000,000 centistokes ("cst"), from about 1,000 cst to about 1,800,000 cst, from about 50,000 cst to about 1,500,000 cst, or even from about 100,000 cst to about 1,500,000 csk.

The dispersed silicone compounds typically have a number average particle diameter ranging from about 0.01 µm to about 50 µm. For small particle application to hair, the number average particle diameters typically range from about 0.01 µm to about 4 µm, from about 0.01 µm to about 2 µm, or even from about 0.01 µm to about 0.5 µm. For larger particle application to hair, the number average particle diameters typically range from about 4 µm to about 50 µm, from about 6 µm to about 30 µm, from about 9 µm to about 20 µm, or even from about 12 µm to about 18 µm.

a. Silicone Oils

Silicone fluids may include silicone oils, which are flowable silicone materials having a viscosity, as measured at 25° C., less than 1,000,000 cst, from about 5 cst to about 1,000,000 cst, or even from about 100 cst to about 600,000 cst. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

b. Amino and Cationic Silicones

Silicone compounds of the present invention may include an aminosilicone. Aminosilicones, as provided herein, are silicones containing at least one primary amine, secondary amine, tertiary amine, or a quaternary ammonium group. Useful aminosilicones may have less than about 0.5% nitrogen by weight of the aminosilicone, less than about 0.2%, or even less than about 0.1%. Higher levels of nitrogen (amine functional groups) in the amino silicone tend to result in less friction reduction and consequently less conditioning benefit from the aminosilicone. It should be understood that in some product forms, higher levels of nitrogen are acceptable in accordance with the present invention.

In one aspect, the aminosilicones used in the present invention have a particle size of less than about 50µ once incorporated into the final composition. The particle size measurement is taken from dispersed droplets in the final composition. Particle size may be measured by means of a laser light scattering technique, using a Horiba model LA-930 Laser Scattering Particle Size Distribution Analyzer (Horiba Instruments, Inc.).

In one embodiment, the aminosilicone typically has a viscosity of from about 1,000 cst (centistokes) to about 1,000,000 cst, from about 10,000 to about 700,000 cst, from about 50,000 cst to about 500,000 cst, or even from about 100,000 cst to about 400,000 cst. This embodiment may also comprise a low viscosity fluid, such as, for example, those materials described below in Section F.(1). The viscosity of aminosilicones discussed herein is measured at 25° C.

In another embodiment, the aminosilicone typically has a viscosity of from about 1,000 cst to about 100,000 cst, from about 2,000 cst to about 50,000 cst, from about 4,000 cst to about 40,000 cst, or even from about 6,000 cst to about 30,000 cs.

In one embodiment, the aminosilicone is contained in the composition of the present invention at a level by weight of from about 0.05% to about 20%, from about 0.1% to about 10%, and or even from about 0.3% to about 5%.

c. Silicone Gums

Other silicone compounds suitable for use in the compositions of the present invention are the insoluble silicone gums. These gums are polyorganosiloxane materials having a viscosity, as measured at 25° C., of greater than or equal to 1,000,000 csk. Specific non-limiting examples of silicone gums for use in the compositions of the present invention include polydimethylsiloxane, (polydimethylsiloxane)(methylvinylsiloxane) copolymer, poly(dimethylsiloxane)(diphenyl siloxane)(methylvinylsiloxane) copolymer and mixtures thereof.

d. High Refractive Index Silicones

Other non-volatile, insoluble silicone fluid compounds that are suitable for use in the compositions of the present invention are those known as "high refractive index silicones," having a refractive index of at least about 1.46, at least about 1.48, m at least about 1.52, or even at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

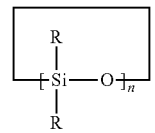

wherein R is as defined above, and n is a number from about 3 to about 7, or even from about 3 to about 5.

Silicone fluids suitable for use in the compositions of the present invention are disclosed in U.S. Pat. Nos. 2,826,551, 3,964,500, and 4,364,837.

e. Silicone Resins

Silicone resins may be included in the conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

In one aspect, silicone resins for use in the compositions of the present invention include, but are not limited to MQ, MT, MTQ, MDT and MDTQ resins. In one aspect, Methyl is a highly suitable silicone substituent. In another aspect, silicone resins are typically MQ resins, wherein the M:Q ratio is typically from about 0.5:1.0 to about 1.5:1.0 and the average molecular weight of the silicone resin is typically from about 1000 to about 10,000.

f. Modified Silicones or Silicone Copolymers

Other modified silicones or silicone copolymers are also useful herein. Examples of these include silicone-based quaternary ammonium compounds (Kennan quats) disclosed in U.S. Pat. Nos. 6,607,717 and 6,482,969; end-terminal quaternary siloxanes; silicone aminopolyalkyleneoxide block copolymers disclosed in U.S. Pat. Nos. 5,807,956 and 5,981,681; hydrophilic silicone emulsions disclosed in U.S. Pat. No. 6,207,782; and polymers made up of one or more crosslinked rake or comb silicone copolymer segments disclosed in U.S. Pat. No. 7,465,439. Additional modified silicones or silicone copolymers useful herein are described in US Patent Application Nos. 2007/0286837A1 and 2005/0048549A1.

In alternative embodiments of the present invention, the above-noted silicone-based quaternary ammonium compounds may be combined with the silicone polymers described in U.S. Pat. Nos. 7,041,767 and 7,217,777 and US Application number 2007/0041929A1.

2. Organic Conditioning Oils

The compositions of the present invention may also comprise from about 0.05% to about 3%, from about 0.08% to about 1.5%, or even from about 0.1% to about 1%, of at least one organic conditioning oil as the conditioning agent, either alone or in combination with other conditioning agents, such as the silicones (described herein). Suitable conditioning oils include hydrocarbon oils, polyolefins, and fatty esters. Suitable hydrocarbon oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils are typically from about $C_{12}$ to about $C_{19}$. Branched chain hydrocarbon oils, including hydrocarbon polymers, typically will contain more than 19 carbon atoms. Suitable polyolefins include liquid polyolefins, liquid poly-α-olefins, or even hydrogenated liquid poly-α-olefins. Polyolefins for use herein may be prepared by polymerization of $C_4$ to about $C_{14}$ or even $C_6$ to about $C_{12}$. Suitable fatty esters include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

3. Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217,914, 4,381,919, and 4,422,853.

F. Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, or even from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (*Cyclonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein include Carbomers with trade names Carbopol® 934, Carbopol® 940, Carbopol® 950, Carbopol® 980, and Carbopol® 981, all available from B.F. Goodrich Company, acrylates/steareth-20 methacrylate copolymer with trade name ACRYSOL™ 22 available from Rohm and Hass, nonoxynyl hydroxyethylcellulose with trade name Amercell™ POLYMER HM-1500 available from Amerchol, methylcellulose with trade name BENECEL®, hydroxyethyl cellulose with trade name NATROSOL®, hydroxypropyl cellulose with trade name KLUCEL®, cetyl hydroxyethyl cellulose with trade name POLYSURF® 67, all supplied by Hercules, ethylene oxide and/or propylene oxide based polymers with trade names CARBOWAX® PEGs, POLYOX WASRs, and UCON® FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855.

These suspending agents include ethylene glycol esters of fatty acids in one aspect having from about 16 to about 22 carbon atoms. In one aspect, useful suspending agents include ethylene glycol stearates, both mono and distearate, but in one aspect, the distearate containing less than about 7% of the mono stearate. Other suitable suspending agents include alkanol amides of fatty acids, having from about 16 to about 22 carbon atoms, or even about 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® R available from Rheox, Inc. Long chain acyl derivatives, ethylene glycol esters of long chain carboxylic acids, long chain amine oxides, and alkanol amides of long chain carboxylic acids in addition to the materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

G. Gel Matrix

The above cationic surfactants, together with high melting point fatty compounds and an aqueous carrier, may form a gel matrix in the composition of the present invention.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, from about 1:1 to about 1:10, or even from about 1:1 to about 1:6.

The formulations of the present invention can be in the form of pourable liquids (under ambient conditions). Such compositions will therefore typically comprise a carrier, which is present at a level of from about 20% to about 95%, or even from about 60% to about 85%. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in the present invention includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Method of Making Conditioner Formulations

The hair conditioners can be prepared by any conventional method well known in the art. They are suitably made as follows: deionized water is heated to 85° C. and cationic surfactants and high melting point fatty compounds are mixed in. If necessary, cationic surfactants and fatty alcohols can be pre-melted at 85° C. before addition to the water. The water is maintained at a temperature of about 85° C. until the components are homogenized, and no solids are observed. The mixture is then cooled to about 55° C. and maintained at this temperature, to form a gel matrix. Silicones, or a blend of silicones and a low viscosity fluid, or an aqueous dispersion of a silicone is added to the gel matrix. When included, poly alpha-olefin oils, polypropylene glycols, and/or polysorbates are also added to the gel matrix. When included, other additional components such as perfumes and preservatives are added with agitation. The gel matrix is maintained at about 50° C. during this time with constant stiffing to assure homogenization. After it is homogenized, it is cooled to room temperature. A triblender and/or mill can be used in each step, if necessary to disperse the materials.

Method of Manufacture

The conditioner compositions of the present invention can be prepared by the process comprising: 1) coating a polyacrylate microcapsule with an anionic emulsifier to form an anionic polyacrylate microcapsule; 2) combining the anionic polyacrylate microcapsule with a deposition aid selected from the group consisting of cationic deposition polymer, aminosilicone, and combinations thereof, to form a premix; and 3) adding the premix to a conditioner agent and a carrier.

In another embodiment, the conditioner compositions of the present invention can be prepared by the process comprising: 1) coating a polyacrylate microcapsule with an anionic emulsifier to form an anionic polyacrylate microcapsule; 2) combining the anionic polyacrylate microcapsule with a deposition aid selected from the group consisting of cationic deposition polymer, aminosilicone, and mixtures thereof, to form a premix; 3) adding the premix to a anionic surfactant; and 4) adding the resulting composition of step (3) to a conditioner agent and a carrier.

It has been unexpectedly found that the association of an anionic polyacrylate microcapsule with a deposition aid has a higher viscoelasticity than in the absence of the mixed components thus giving a better adhesion of the anionic microcapsules to the hair.

For example, when an anionic emulsifier comprising a copolymer of acrylic acid and butyl acrylate (molecular weight of 40,000 g/mol), is mixed with various cationic polymers to form a polymer premix, the result is a significant increase in viscoelasticity. This increase indicates a strong polyelectrolyte interaction which is exemplified in the increase in viscoelastic component G' as the quantity of cationic polymer increases (See Table 1)

TABLE 1

Viscoelasticity as a function of anionic:cationic polymer premix ratio.

| Sample Description | Anionic Emulsifier (wt %) | Cationic Polymer (wt %) | Anionic Surfactant (wt %) | G' at 1 Hz (Pascals) | G" at 1 Hz (Pascals) |
|---|---|---|---|---|---|
| 1:5 Anionic:Cationic | 5.10% | 25.48% | 0.00% | 0.369 | 6.55 |
| 1:10 Anionic:Cationic | 2.78% | 27.79% | 0.00% | 0.178 | 7.22 |
| 1:20 Anionic:Cationic | 1.46% | 29.12% | 0.00% | 0.233 | 7.92 |

Furthermore, when an anionic surfactant is added to the polymer premix, a substantial increase in viscoelasticity is also noted. Such an increase in viscoelasticity is influenced by the strength of the association between the cationic deposition polymer and the anionic surfactant. This is exemplified in the increase in viscoelastic component G' upon addition of anionic surfactant to the premix (See Table 2).

TABLE 2

Viscoelasticity as a function of anionic surfactant addition to polymer premix.

| Sample ID | Anionic Emulsifier | Cationic Polymer | Anionic Surfactant | G' at 1 Hz (Pascals) | G" at 1 Hz (Pascals) |
|---|---|---|---|---|---|
| 1:5 Anionic:Cationic | 3.05% | 15.25% | 10.87% | 42 | 105.6 |
| 1:10 Anionic:Cationic | 1.65% | 16.48% | 11.74% | 37.1 | 7.1 |
| 1:20 Anionic:Cationic | 0.86% | 17.17% | 12.23% | 118.2 | 133.9 |

In one embodiment of the invention, an anionic emulsifier is covalently bonded to the outer wall of the polyacrylate microcapsule by incorporating the anionic emulsifier during the microcapsule making process. In another embodiment, the anionic emulsifier is added to the slurry comprising a fully formed polyacrylate microcapsule. After forming the anionic polyacrylate microcapsule through either step, a cationic deposition polymer is then added to the anionic microcapsule to form a viscoelastic premix. When this premix is then combined with an anionic surfactant, an association of polymers forms a microstructure on the anionic polyacrylate microcapsule wall. The microstructure forms even upon dilution of the conditioner composition. Once formed, the high viscosity of the polymer association microstructure results in an anionic polyacrylate microcapsule that maintains its microcapsule structure even upon dilution of the conditioner composition. In addition, the microcapsule structure provides multiple points of contact to the substrate which works to increase the amount of time the microcapsule is on the hair.

The polyacrylate microcapsules of the present invention can be formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; 5,486,303 all of which are incorporated herein by reference.

Product Forms

The conditioner compositions of the present invention can be in the form of rinse-off products or leave-on products, and can be formulated in a wide variety of product forms, including but not limited to creams, gels, emulsions, mousses and sprays.

In one embodiment, the conditioner composition is in the form of a gel comprising less than about 45% water. In such embodiment, the gel may have a neat viscosity of about 1,000 cps to about 10,000 cps. The neat viscosity of a gel can be defined as the viscosity of the fluid at a shear rate of 1/sec. Scientifically, viscosity is the ratio of shear stress to shear rate. In some embodiments, the range of shear rates for gels is from 0.01/sec to 10/sec.

Neat viscosity of the gel product form can be measured with a rheometer according to the following method:
(1) Load the sample onto the plate.
(2) Establish a gap of 1 millimeter between the 1 degree cone and the plate.
(3) Perform a shear sweep on the fluid from 0.01/sec to 10/sec.
(4) Record the shear stress response of the fluid.
(5) Determine the neat viscosity of the fluid by calculating the ratio of shear stress to shear rate at each shear rate.

TEST METHODS

It is understood that the test methods that are disclosed in the Test Methods Section of the present application should be used to determine the respective values of the parameters of Applicants' invention as such invention is described and claimed herein.

A. C log P

The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor, and C. A. Ramsden, Eds. P. 295, Pergamon Press, 1990, incorporated herein by reference). C log P values may be calculated by using the "C LOG P" program available from Daylight Chemical Information Systems Inc. of Irvine, Calif. U.S.A.

B. Boiling Point

Boiling point is measured by ASTM method D2887-04a, "Standard Test Method for Boiling Range Distribution of Petroleum Fractions by Gas Chromatography," ASTM International.

C. Median Particle Size

Particle size is measured using an Accusizer 780A, made by Particle Sizing Systems, Santa Barbara Calif. The instrument is calibrated from 0 to 300μ using Duke particle size standards. Samples for particle size evaluation are prepared by diluting about 1 g of capsule slurry in about 5 g of deionized water and further diluting about 1 g of this solution in about 25 g of water.

About 1 g of the most dilute sample is added to the Accusizer and the testing initiated, using the autodilution feature. The Accusizer should be reading in excess of 9200 counts/second. If the counts are less than 9200 additional sample should be added. The accusizer will dilute the test sample until 9200 counts/second and initiate the evaluation. After 2 minutes of testing the Accusizer will display the results, including volume-weighted median size.

The broadness index can be calculated by determining the particle size at which 95% of the cumulative particle volume is exceeded (95% size), the particle size at which 5% of the cumulative particle volume is exceeded (5% size), and the median volume-weighted particle size (50% size—50% of the particle volume both above and below this size). Broadness Index (5)=((95% size)–(5% size)/50% size).

D. Olfactive Analysis of Conditioner Product

Analysis steps include:
a. 0.4 milliliters of Conditioner product is applied to a hair switch (IHI, 4 grams, 8 inches long, moderately damaged grade) that has been combed, wet, and lightly squeeged. Lather switch 50-60 strokes (30 seconds) in a milking action.
b. Rinse with stationary shower rinse with no manipulation of hair (100 degrees Fahrenheit water temperature, water flow at 1.5 gallons per minute, for 30 seconds, water hardness of 8 grains per gallon). Lightly squeegee once down the hair switch from top to bottom between fingers after rinsing to remove excess water.
c. Leave hair to dry at ambient temperature by hanging it on a rack. After approximately 3 hours, olfactively grade the hair switch according to the Primavera Grade (0-100 scale for intensity, where a 10 point difference is consumer noticeable). Record this as the Initial Pre-Comb fragrance intensity.
d. Comb the hair switch 3 times and olfactively grade, record this as the Initial Post-Comb fragrance intensity.
e. Leave the hair switch under ambient conditions (70 degrees Fahrenheit and 30% relative humidity) for 24 hours. Then, olfactively grade the hair switch according to the Primavera Grade (0-100 scale for intensity, where a 10 point difference is consumer noticeable), record this as the 24 hr aged Pre-Comb olfactive intensity. Comb the hair switch 3 times and assign an olfactive grade, record this as the 24 hr aged Post-Comb olfactive intensity.

E. Fracture Strength Test Method

Analysis steps include:
a.) Place 1 gram of particles in 1 liter of distilled deionized (DI) water.
b.) Permit the particles to remain in the DI water for 10 minutes and then recover the particles by filtration, using a 60 mL syringe filter, 1.2 micron nitrocellulose filter (Millipore, 25 mm diameter).
c.) Determine the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the fracture strength of each particle by dividing the rupture force (in Newtons) by the cross-sectional area of the respective spherical particle ($\pi r^2$, where r is the radius of the particle before compression), said cross-sectional area being determined as follows: measuring the particle size of each individual particle using the experimental apparatus and method of Zhang, Z.; Sun, G; "Mechanical Properties of Melamine-Formaldehyde microcapsules," J. Microencapsulation, vol 18, no. 5, pages 593-602, 2001.

d.) Use the 50 independent measurements from c.) above, and calculate the percentage of particles having a fracture strength within the claimed range fracture strength range.

F. Zeta Potential
(1) Equipment specifications: Malvern Zeatasizer Nano Model ZEN3600 Sample cell, disposable capillary cell (green cell)
(2) Use Duke standards to measure the PSD, and use it to measure the zeta potential to assure that the instrument is functioning properly.
(3) Flush a DTS1060 capillary cell with 1-2 mL ethanol, the with DI water to prepare the capillary cell.
(4) Sample preparation: first, filter 20 mL DI water through 0.2 micron filter into a 20 mL vial. Add 1 drop (50 microliters of 30 wt % solids particular suspension into the vial and invert the sample back and forth gently until the particulate suspension is homogeneously dispersed in the vial. Next, rinse a DTS1060 green disposable zeta cell with 1-2 mL of DI water, then use a syringe to transfer the sample solution from the vial into the zeta cell, making sure that no air bubbles are present in the cell. Fill the cell to the top, then place a cap on the cell outlet and inlet (again making sure no air bubbles are present in the sample cell). Then, place the cell in the sample chamber, with the electrodes facing the sides of the system. Finally, place the sample cell in the instrument.
(5) Conditions for the run:
  a. Refractive index=1.35 (this number may vary for suspensions. One can measure the refractive index for any particulate suspension using a refractometer)
  b. Temperature=25 degrees Centigrade
  c. Equilibration time=1 minute
  d. Smoluchowski model to be used to calculate the zeta potential
(6) Measure each sample in triplicate. The result from the instrument is reported as Zeta Potential in milliVolts, with no extrapolation.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

A perfume composition, called Scent A, is utilized to prepare the examples of the invention. The table below lists the ingredients, and their properties. Table 2 provides the C log P breakdown of the perfume oil composition.

TABLE 1

| Material Name | ClogP | Boiling Point ° C. |
|---|---|---|
| Beta Gamma Hexenol | 1.3 | 155 |
| Phenyl Ethyl Alcohol | 1.32 | 219 |
| Helional | 1.77 | 329 |

TABLE 1-continued

| Material Name | ClogP | Boiling Point ° C. |
|---|---|---|
| Triplal Extra | 1.78 | 199 |
| Amyl- Acetate (isomer Blends) | 1.87 | 135 |
| Melonal | 2.09 | 182 |
| Liffarome | 2.14 | 167 |
| Iso Eugenol Acetate | 2.17 | 303 |
| Cis 3 Hexenyl Acetate | 2.18 | 167 |
| Jasmolactone | 2.36 | 219 |
| 2'6-nonadien-1-ol | 2.43 | 213 |
| Florasa | 2.46 | 238 |
| Nonalactone | 2.66 | 193 |
| Cis Jasmone | 2.81 | 254 |
| Ethyl Linalool | 2.92 | 223 |
| Pino Acetaldehyde | 2.98 | 261 |
| Methyl Dihydro Jasmonate | 3.01 | 323 |
| Undecavertol | 3.06 | 242 |
| Azurone 10/tec 0015573 | 3.06 | 395 |
| Dihydro Myrcenol | 3.08 | 195 |
| Cyclemax | 3.23 | 281 |
| Hivernal | 3.29 | 351 |
| Pomarose | 3.51 | 214 |
| Undecalactone | 3.75 | 228 |
| Damascenone Total 937459 | 3.89 | 267 |
| Acalea (01-1963) | 3.9 | 344 |
| Cis-3-hexenyl Salicylate | 4 | 316 |
| Ionone Beta | 4.02 | 267 |
| Polysantol | 4.21 | 256 |
| Ambroxan | 4.58 | 285 |
| 5-cyclohexadecen-1-one | 5.04 | 331 |
| Iso E Super Or Wood | 5.05 | 325 |
| Laevo Muscone | 5.48 | 321 |
| Helvetolide 947650 | 5.56 | 309 |

Example 1

Nonionic Microcapsule (TAS0810101, MVF1837-94B)

An oil solution, consisting of 75 g Fragrance Oil Scent A, 75 g of Isopropyl Myristate, 0.6 g DuPont Vazo-52, and 0.4 g DuPont Vazo-67, is added to a 35° C. temperature controlled steel jacketed reactor, with mixing at 1000 rpm (4 tip, 2" diameter, flat mill blade) and a nitrogen blanket applied at 100 cc/min. The oil solution is heated to 75° C. in 45 minutes, held at 75° C. for 45 minutes, and cooled to 60° C. in 75 minutes.

A second oil solution, consisting of 37.5 g Fragrance Oil, 0.5 g tertiarybutylaminoethyl methacrylate, 0.4 g 2-carboxyethyl acrylate, and 20 g Sartomer CN975 (hexafunctional urethane-acrylate oligomer) is added when the first oil solution reached 60° C. The combined oils are held at 60° C. for an additional 10 minutes.

Mixing is stopped and a water solution, consisting of 56 g of 5% active polyvinyl alcohol Celvol 540 solution in water, 244 g water, 1.1 g 20% NaOH, and 1.2 g DuPont Vazo-68WSP, is added to the bottom of the oil solution, using a funnel.

Mixing is again started, at 2500 rpm, for 60 minutes to emulsify the oil phase into the water solution. After milling is completed, mixing is continued with a 3" propeller at 350 rpm. The batch is held at 60° C. for 45 minutes, the temperature is increased to 75° C. in 30 minutes, held at 75° C. for 4 hours, heated to 90° C. in 30 minutes and held at 90° C. for 8 hours. The batch is then allowed to cool to room temperature.

The finished microcapsules have a median particle size of 6.4 microns, a broadness index of 1.3, and a zeta potential of negative 0.5 millivolts.

Example 2

Anionic Microcapsule, Large Particle Size (TAS1122101)

Capsules are made using identical materials, compositions, and process conditions as in Example 1 with the following exceptions: 1 gram of Vazo-52, 0.8 grams of Vazo-67, 0.3 grams of tertiarybutylaminoethyl methacrylate, 0.25 grams of 2-carboxyethyl acrylate, and 12 grams of Sartomer CN975 as compositional differences in the oil phase; and 22 grams of 25% active Colloid 351, and 308 grams of water as compositional differences in the water phase. All other mixing and process conditioners remain the same.

The finished microcapsules have a median particle size of 10.7 microns, a broadness index of 1.5, and a zeta potential of negative 60 milivolts.

Example 3

Anionic Microcapsule, Small Particle Size (TAS1123101)

Capsules are made using identical materials, compositions, and process conditions as in Example 1 with the following exceptions: 1 gram of Vazo-52, 0.8 grams of Vazo-67, 1.5 grams of tertiarybutylaminoethyl methacrylate, 1.2 grams of 2-carboxyethyl acrylate, and 60 grams of Sartomer CN975 as compositional differences in the oil phase; and 68 grams of 25% active Colloid 351, and 282 grams of water as compositional differences in the water phase. All other mixing and process conditioner sremain the same.

The finished microcapsules have a median particle size of 1.4 microns, a broadness index of 1.2, and a zeta potential of negative 60 milivolts.

Example 4

Rinse-off Conditioner Making

The following procedure is used to make a 500 gram batch of rinse-off conditioner. 14.24 grams of Genamin KDMP flakes are added to 410 grams of preheated water at 95 degrees Centigrade, in a 1 liter stainless steel vessel that is submerged in a water bath at 92 degrees Centigrade. The contents of the 1 liter vessel is held under agitation at 350 RPM using a IKA mixer, and a turbine agitator. A transparent solution is obtained after 5 minutes. Then, 9.3 grams of cetyl alcohol flakes, and 23.2 grams of stearyl alcohol flakes are added to the stainless steel vessel, with temperature of the contents controlled to 75-85 degrees Centigrade. Agitation is increased to 500 RPM. After 10 minutes, the following ingredients are added to the stainless steel vessel: 0.64 grams of Dissolvine EDTA acid, 6.8 grams of a 1 wt % sodium hydroxide solution, 2 g of Benzyl Alcohol, and 0.17 grams of Kathon CG preservative (methylchloroisothiazolinone and methylisothiazolinone). The contents are mixed for 2 minutes. The stainless steel reactor is then removed from the constant temperature water bath, and then the contents are cooled to 60 degrees centigrade using a cold water bath. The stainless steel reactor is placed under a IKA mill. 17.5 grams of Aminosilicone (Momentive Performance Chemicals, viscosity of 10,000 mPa·s) is premixed with 5.0 grams of the microcapsules of Example 5, and then slowly added to the stainless steel vessel, with the mill operating at 20,000 RPM. A spatula is used to assure that all of the material is overturned in the vessel. Milling is continued for 7 minutes at 55 degrees Centigrade. Finally, 0.25 grams of panthenyl ethyl ether and 0.50 grams of panthenol are added to the vessel, and agitated for 2 minutes. The conditioner viscosity and microstructure are characterized to assure that the conditioner formulation meets product design specifications.

Example 5

Conditioner with No Premixing of Capsules

Perfume and/or perfume microcapsules disclosed in the above examples are added on top of a pre-made conditioner formula with a 3 wt % formula hole of Example 4. The table below lists the masses of the various ingredients. The mixture is then speed mixed at 1900 RPM for 1 minute using a DAFC 400FVZ speed mixer. The Olfactive Analysis of Conditioner Product test method is utilized to grade hair treated with the prepared shampoo compositions. These results are presented below.

| Example Reference | PMC Example ID | Mass of Microcapsule or Perfume (g) | Mass of Rinse-off Conditioner (g) | Mass of Water (g) | 4 hr (Pre/Post-Comb) | 24 hr (Pre/Post-Comb) |
|---|---|---|---|---|---|---|
| 9A | Reference | 0.50 | 97.0 | 2.500 | 20/20 | 10/10 |
| 9B | 1 Nonionic | 1.81 | 97.0 | 1.188 | 10/50 | 10/20+ |
| 9C | 3 Anionic | 2.42 | 97.0 | 0.58 | 10/40 | 10/30+ |

Example 6

Conditioner with Premixing of Capsules

The perfume microcapsules of Example 3 are first premixed with cationic polymers by preweighing the perfume microcapsules in a jar, then adding the cationic polymer. The contents are then mixed at 1950 RPM for 1 minute using a Hausfeld DAFC 400FVZ speed mixer to achieve a homogeneous suspension of microcapsules.

The cationic polymer/microcapsule premixes are then formulated into a conditioner during the conditioner making process described in Example 4. The premix substituted the aminosilicone described in Example 4.

The Olfactive Analysis of Conditioner Product test method is utilized to grade hair treated with the prepared conditioner compositions. These results are presented below.

| Example | Description | Initial (3 hr) (Pre/Post Comb) | 24 hr (Pre/Post Comb) |
|---|---|---|---|
| | Rinse-Off Conditioner | | |
| Reference 10A | Perfume Control—Scent A | 20/20 | 0/0 |
| | Aminosilicone + Anionic PMC of Example 3 Premix added to ROC, Aged 17 days/RT | 20+/40+ | 0/20 |

-continued

| Example | Description | Initial (3 hr) (Pre/Post Comb) | 24 hr (Pre/Post Comb) |
|---|---|---|---|
| | Rinse-Off Conditioner | | |
| 10B | Mirapol AT-1 (49 meq/A) + Anionic PMC of Example 3 Premix added to ROC, no aminosilicone | 35/45 | 0/20+ |
| 10C | Mirapol 100S (162 meq/A) + Anionic PMC of Example 3 premix added to ROC, no aminosilicone | 20+/20+ | 0/10 |
| 10D | Polycare 133 (324 meq/A) + Anionic PMC of Example 3 premix added to ROC, no aminosilicone | 25/25 | 0/10 |

Note that the anionic microcapsules premixed with the aminosilicone and Mirapol AT-1 provides the best fragrance longevity (24 hr) results.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A conditioner composition comprising:
   (a) from about 0.001% to about 10% of an anionic charged polyacrylate microcapsule;
   (b) from about 0.01% to about 2% of a deposition aid selected from the group consisting of cationic deposition polymer, aminosilicone, and combinations thereof; and
   (c) from about 2% to about 25% of a conditioning agent selected from the group consisting of a cationic surfactant, a high melting point fatty compound, a silicone compound, and combinations thereof; and
   (d) a carrier;
   wherein the weight ratio of the anionic charged polyacrylate microcapsule to either the cationic deposition polymer or the aminosilicone is from about 0.5:30 to about 20:1.

2. The conditioner composition of claim 1, wherein the anionic charged polyacrylate microcapsule comprises an anionic emulsifier.

3. The conditioner composition of claim 2, wherein the anionic emulsifier surrounds at least a part of the external surface of the polyacrylate microcapsule, or is physically or chemically bound to the external surface of the polyacrylate microcapsule.

4. The conditioner composition of claim 2, wherein the anionic emulsifier and the polyacrylate microcapsule are mixed such that the weight ratio of the anionic emulsifier to the polyacrylate microcapsule is from about 1.0:40 to about 0.5:5.

5. The conditioner composition of claim 1, wherein the anionic charged polyacrylate microcapsule and the deposition aid are mixed such that the weight ratio of the anionic charged polyacrylate microcapsule to the deposition aid is from about 1.0:0.01 to about 1.0:10.

6. The conditioner composition of claim 2, wherein the anionic emulsifier is selected from the group consisting of: Poly(meth)acrylic acid; copolymers of (meth)acrylic acids and its (meth)acrylates with C1-C22 alkyl; copolymers of (meth)acrylic acids and (meth)acrylamide; and mixtures thereof.

7. The conditioner composition of claim 1, wherein the anionic charged polyacrylate microcapsule has a particle size of from about 2 microns to about 80 microns.

8. The conditioner composition of claim 2, wherein the polyacrylate microcapsule has a core and a shell that encapsulates said core.

9. The conditioner composition of claim 8, wherein the core comprises from about 6% to about 99.9% of a benefit agent.

10. The conditioner composition of claim 9, wherein the benefit agent is selected from the group consisting of perfumes; brighteners; enzymes; perfume delivery system; conditioning agents; moisturizers; anti-microbial agents; thickeners; sensates; attractants; dyes; pigments; bleaches; and mixtures thereof.

11. The conditioner composition of claim 1, wherein the cationic deposition polymer is selected from the group consisting of starches, guar, cellulose, cassia, locust bean, Konjac, Tara, galactomanna, polyDADMAC, Tapioca starch, and polyTriquat.

12. The conditioner composition of claim 1, wherein the cationic deposition polymer is a water-soluble polymer with a charge density of from about 0.5 milliequivalents per gram to about 12 milliequivalents per gram, and wherein the cationic deposition polymer has a molecular weight of about 100,000 Daltons to about 5,000,000 Daltons.

13. The conditioner composition of claim 1, wherein the deposition aid comprises an aminosilicone.

14. The conditioner composition of claim 1, wherein the carrier comprises water and water solutions of lower alkyl alcohols and polyhydric alcohols.

15. The conditioner composition of claim 1, wherein the anionic charged polyacrylate microcapsule is contained in an agglomerate, and wherein the agglomerate comprises materials selected from the group consisting of silicas, citric acid, sodium carbonate, sodium sulfate, sodium chloride, and binders such as sodium silicates, modified celluloses, polyethylene glycols, polyacrylates, polyacrylic acids, zeolites, and mixtures thereof.

16. The conditioner composition of claim 1, wherein the conditioner composition is in the form of a gel, and wherein the gel comprises less than about 45% water.

17. The conditioner composition of claim 2, wherein the anionic emulsifier and the polyacrylate microcapsule are mixed such that the weight ratio of the anionic emulsifier to the polyacrylate microcapsule is from about 1.0:200 to about 1:20.

18. The conditioner composition of claim 2, wherein the anionic emulsifier and the polyacrylate microcapsule are mixed such that the weight ratio of the anionic emulsifier to the polyacrylate microcapsule is from about 1.0:1000 to about 2:5.

19. The conditioner composition of claim 2, wherein the anionic emulsifier is selected from the group consisting of: carboxyvinylpolymer; acrylate copolymers; Acrylic acid/vinyl ester copolymer/Acrylates/Vinyl Isodecanoate crosspolymer; Acrylates/Palmeth-25 Acrylate copolymer; Acrylate/Steareth-20 Itaconate copolymer; Acrylate/Ceteth-20 Itaconate copolymer; Polystyrene sulphonate; copolymers of methacrylic acid and acrylamidomethylpropane sulfonic acid; copolymers of acrylic acid and acrylamidomethylpropane sulfonic acid; carboxymethycellulose; carboxy guar; copolymers of ethylene and maleic acid; acrylate silicone polymer; and mixtures thereof.

* * * * *